US009278943B2

(12) United States Patent
Leblond et al.

(10) Patent No.: US 9,278,943 B2
(45) Date of Patent: *Mar. 8, 2016

(54) METHODS OF USING AS ANALGESICS 1-BENZYL-1-HYDROXY-2,3-DIAMINO-PROPYL AMINES, 3-BENZYL-3-HYDROXY-2-AMINO-PROPIONIC ACID AMIDES AND RELATED COMPOUNDS

(75) Inventors: Bertrand Leblond, Paris (FR); Eric Beausoleil, Paris (FR); Thierry Taverne, St. Martin Boulogne sur Mer (FR); John E. Donello, Dana Point, CA (US); Fabien (Jacques) Schweighoffer, Fontenay sous Bois (FR)

(73) Assignees: Exonhit Therapeutics SA, Paris (FR); Allergan, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/450,854

(22) Filed: Apr. 19, 2012

(65) Prior Publication Data
US 2012/0225881 A1 Sep. 6, 2012

Related U.S. Application Data

(62) Division of application No. 11/814,604, filed as application No. PCT/US2006/002505 on Jan. 25, 2006, now abandoned.

(60) Provisional application No. 60/647,271, filed on Jan. 26, 2005.

(51) Int. Cl.
| A61K 31/535 | (2006.01) |
| A61K 31/40 | (2006.01) |
| C07D 265/30 | (2006.01) |
| A61K 31/4025 | (2006.01) |
| A61K 31/5375 | (2006.01) |
| C07D 213/64 | (2006.01) |
| C07D 295/12 | (2006.01) |
| C07D 319/18 | (2006.01) |
| A61K 31/4409 | (2006.01) |
| A61K 31/4439 | (2006.01) |
| A61K 31/4545 | (2006.01) |
| A61K 31/4709 | (2006.01) |
| A61K 31/496 | (2006.01) |
| A61K 31/5377 | (2006.01) |
| A61K 31/541 | (2006.01) |

(52) U.S. Cl.
CPC ............. *C07D 265/30* (2013.01); *A61K 31/40* (2013.01); *A61K 31/4025* (2013.01); *A61K 31/4409* (2013.01); *A61K 31/4439* (2013.01); *A61K 31/4545* (2013.01); *A61K 31/4709* (2013.01); *A61K 31/496* (2013.01); *A61K 31/5375* (2013.01); *A61K 31/5377* (2013.01); *A61K 31/541* (2013.01); *C07D 213/64* (2013.01); *C07D 295/12* (2013.01); *C07D 319/18* (2013.01)

(58) Field of Classification Search
None
See application file for complete search history.

(56) References Cited

U.S. PATENT DOCUMENTS

| 5,767,121 A | 6/1998 | Takatani et al. |
| 5,916,911 A | 6/1999 | Shayman et al. |
| 5,945,442 A | 8/1999 | Shayman et al. |
| 5,952,370 A | 9/1999 | Shayman et al. |
| 5,976,781 A | 11/1999 | Haldar et al. |
| 6,030,995 A | 2/2000 | Shayman et al. |
| 6,051,598 A | 4/2000 | Shayman et al. |
| 6,407,064 B2 | 6/2002 | Masuda et al. |
| 2002/0198240 A1 | 12/2002 | Shayman et al. |
| 2003/0050299 A1 | 3/2003 | Hirth et al. |
| 2003/0153768 A1 | 8/2003 | Hirth |

FOREIGN PATENT DOCUMENTS

| EP | 0 720 852 | 7/1996 |
| EP | 0 765 865 | 4/1997 |
| EP | 782992 | 9/1997 |
| JP | 9-216858 | 1/1997 |
| JP | 10324671 | 12/1998 |
| WO | WO 95/05177 | 2/1995 |
| WO | WO 0104108 | 1/2001 |
| WO | WO 01/38228 | 5/2001 |
| WO | WO 01/47874 | 7/2001 |
| WO | WO 0212185 | 2/2002 |
| WO | WO 02062777 | 8/2002 |
| WO | WO 03008399 | 1/2003 |
| WO | WO 03045928 | 5/2003 |
| WO | WO 2005/063275 | 7/2005 |

OTHER PUBLICATIONS

Williams et al (Foye's Principles of Medicinal Chemistry, 5th Edition, pp. 59-63, 2002).*
Patani et al (Chem Rev 96:3147-3176, 1996).*
Kastron, et al. Latvijas PSR Zinatnu Akademijas Vestis, Kimijas Serija (1965) (4), 471-7.
Vlasenko, et al., "Study of the Anesthetic Properties of Beta Amino Alcohols," Biologicheskii Zhurmal Armenii, vol. 28, No. 11, pp. 18-20, 1975.
Shin, S. et al, "Stereoselective synthesis of enantiomerically pure D-threo-PDMP; manipulation of a core 2,3- diamino alcohol unit", *Tetrahedron asymmetry*, 11, 3293-3301, 2000].
Kurosawa et al, "C-Labeling of a Novel Atypical β-Adrenoceptor Agonist, SLM-11044" Journal of Labelled Compounds & Radiopharmaceuticals (1996), 38(3).
Vunam, R. R. et al, "Analogs of ceramide that inhibit glucocerebroside synthetase in mouse brain", *Chem. Phys. Lipids*, 26, 265-278, 1980.
Slavish., J. P. et al, "New PDMP analogues inhibit process outgrowth in an insect cell line", *Bioorg. Med. Chem. Lett.*, 14, 1487-1490, 2004.
Mizutani A. et al, "Effects of Glucosylceramide Synthase Inhibitor and Ganglioside GQ1b on Synchronous Oscillations of Intracellular Ca2+ in Cultured Cortical Neurons", Biochem. Biophys. Res. Commun., 222, 494-498, 1996.
Abe, A. et al, "Structural and stereochemical studies of potent inhibitors of glucosylceramide synthase and tumor cell growth", J. Lipid Res. 36, 611-621, 1995.
Radin, A. et al, "Use of an Inhibitor of Glucosylceramide Synthesis, D-1-Phenyl-2-decanoylamino-3-morpholino-1-propanol", NeuroProtocols, 3(2), 145-55, 1993.
Nishida, A., "Practical Synthesis of threo-(1S, 2S)- and erythro-(1R, 2S)-1-Phenyl-2-palmitoylamino-3-morpholino-l-propanol (PPMP) from L-Serine", *Synlett*, 4, 389-390, 1998.

Miura, T. et al, "Synthesis and Evaluation of Morpholino- and Pyrrolidinosphingolipids as Inhibitors of Glucosylceramide Synthatse", Bioorg. Med. Chem., 6, 1481-1498, 1998.
Mitchell et al, "Glycosyltransferase Inhibitors: Synthesis of D-threo-PDMP, L-threo-PDMP, and Other Brain Glucosylceramide Synthase Inhibitors from D- or L-Serine", *J. Org. Chem.*, 63 (24), 8837-8842, 1998.
Jimbo M. et al, "Development of a New Inhibitor of Glucosylceramide Synthase", *J. Biochem.*, 127(3) 485-91, 2000.
Lee, L. et al, "Improved Inhibitors of Glucosylceramide Synthase", *J. Biol. Chem.*, 274, 21, 14662-14669, 1999.
Kim et al, 1992, Pain 150, pp. 355-363.
Inokuchi, J. et al, "Preparation of the active isomer of 1-phenyl-2-decanoylamino-3-morpholino-1-propanol, inhibitor of murine glucocerebroside", *J. Lipid Res.* 28, 565-571, 1987.
Inokuchi et al, "A Synthetic Ceramide Analog (L-PDMP) Up-regulates Neuronal Function", *Ann. N.Y. Acad. Sci.*, 845(1), 219-224, 1998.
Inokuchi J. et al, "Antitumor Activity Via Inhibition of Glycosphingolipid Biosynthesis", *Cancer Letters* 38(1-2), 23-30, 1987.
Husain A. et al, "syn-Selective additions to Garner aldehyde: synthesis of a potent glucosylceramide synthase inhibitor", *Tetrahedron Lett.*, 43, 8621-8623, 2002.
Dixon, W.J., *Ann. Rev. Pharmacol. Toxicol.* 20:441-462 (1980).
Abe, A. et al., "Improved Inhibitors of Glucosylceramide Synthase", *J. Biochem.*, 111, 191-196, 1992.
Tucker et al, "A series of potent HIV-1 protease inhibitors containing a hydroxyethyl secondary amine transition state isostere: synthesis, enzyme inhibition, and antiviral activity" Journal of Medicinal Chemistry, 35 (14), 2525-33, 1992.
Venturella et al, "Synthesis of several derivatives of phenyl(2-hydroxy-3-yrazyl)carbinol", Journal of Pharmaceutical Sciences, vol. 52, No. 2, 142-146, Feb. 1963.
Burford et al, "Pharmacology studies on some new acrylic acid amide derivatives", vol. 54, No. 12, 1750-1754, Dec. 1965.
Bixler et al, "Synthesis of beta-/4-pyridyl)-DL-analine and of beta-/4-pyridyl-1-oxide)-DL-, D-, and L-analine", Journal of Organic Chemistry, vol. 23, pp. 575-584, 1958.
Tabanella et al, "Preparation of enantiomerically pure pyridyl amino acids from serine", Organic & Biomolecular Chemistry, vol. 1, No. 23, pp. 4254-4261, 2003.
Gregory et al, "polypeptides, part VII", Journal of the Chemical Society, pp. 531-540, 1968.
Database Crossfire Beilstein Informationsysteme, XP002380778 Tack et al, Archiv Der Pharmazie, No. 312, pp. 138-147, 1979.
Inokuchi et al, "Amino Alcohol esters as ceramide analogs and pharmaceuticals containing them for treatment of nerve diseases", XP002381282.
Senton, et al., (J Med Chem 46:5005-5014, 2003).
Williams, et al. (Foye's Principles of Biochemistry, pp. 59-61, 2002).
Berge, et al. (J Pharm Sci 66:1-19, 1977).

\* cited by examiner

*Primary Examiner* — Craig Ricci
(74) *Attorney, Agent, or Firm* — Jonathan Bass

(57) ABSTRACT

The compounds shown by the structural formulas below have analgesic effect and are used in compositions and methods for treating mammal in need of such treatment.

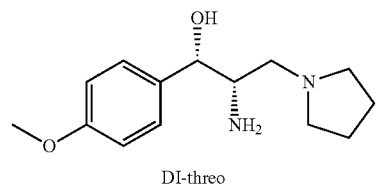

Dl-threo

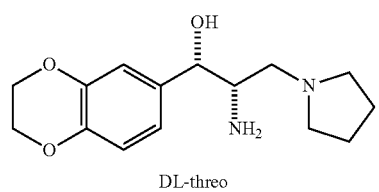

DL-threo

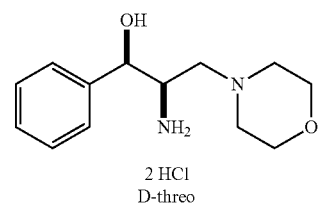

2 HCl
D-threo

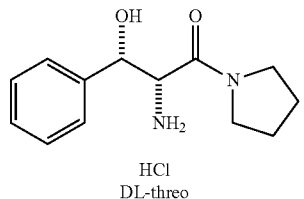

HCl
DL-threo

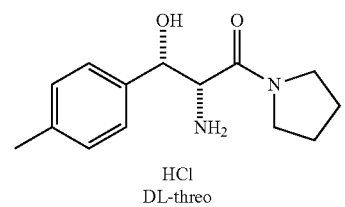

HCl
DL-threo

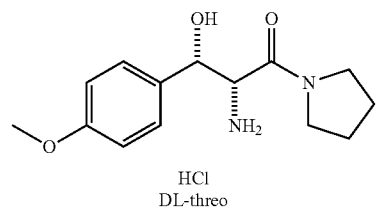

HCl
DL-threo

-continued
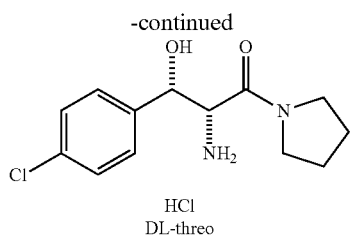
HCl
DL-threo
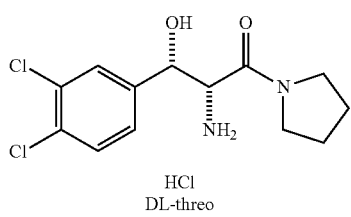
HCl
DL-threo
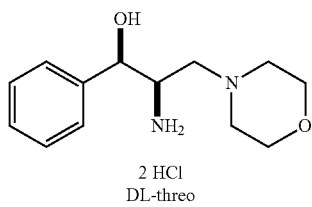
2 HCl
DL-threo
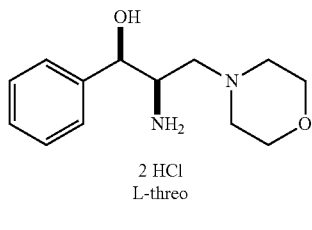
2 HCl
L-threo
-continued
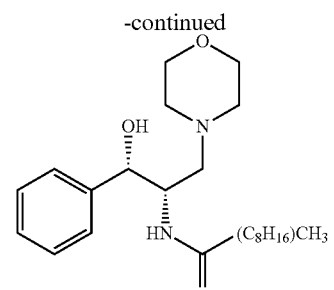
L-threo-PDMP
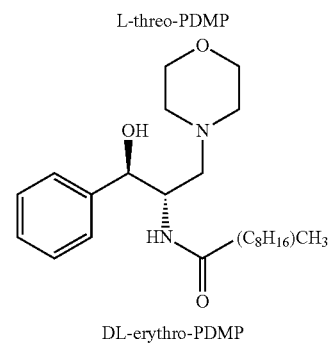
DL-erythro-PDMP
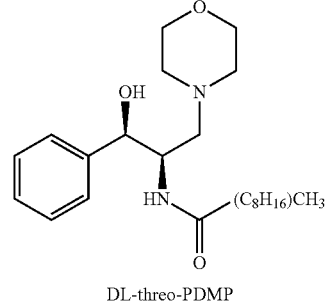
DL-threo-PDMP
12 Claims, No Drawings

METHODS OF USING AS ANALGESICS 1-BENZYL-1-HYDROXY-2, 3-DIAMINO-PROPYL AMINES, 3-BENZYL-3-HYDROXY-2-AMINO-PROPIONIC ACID AMIDES AND RELATED COMPOUNDS

CLAIM OF PRIORITY

This application is a divisional of U.S. application Ser. No. 11/814,604, filed Apr. 2, 2008 now abandoned, which is a national stage application under 35 U.S.C. §371 of PCT application PCT/US2006/002505, filed on Jan. 25, 2006, which claims the benefit of U.S. provisional application Ser. No. 60/647,271, filed on Jan. 26, 2005, all of which are incorporated herein by reference in their entirety.

BACKGROUND OF THE INVENTION

1. Field of the Invention

The present invention relates to methods of treating mammals in need of such treatment with an analgesics composition containing 1-benzyl-1-hydroxy-2,3-diamino-propyl amines, 3-benzyl-3-hydroxy-2-amino-propionic acid amides or related compounds.

2. Background Art

1-Phenyl-2-decanoylamino-3-morpholino-1-propanol (PDMP) was discovered by Vunam, R. R. and Radin, N., *Chem. Phys. Lipids*, 26, 265-278, 1980. Preparation of PDMP is described in Inokuchi, J. et al., *J. Lipid Res.* 28, 565-571, 1987; Radin, A. et al., *NeuroProtocols*, 3(2), 145-55, 1993; Radin, A. et al., *J. Lipid Res.* 36, 611-621, 1995 and U.S. Pat. No. 5,916,911.

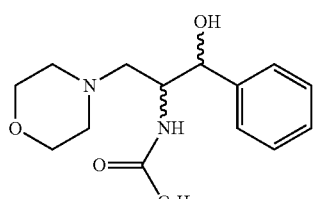

PDMP
mixture of DL-erythro and
DL-threo isomers

These derivatives inhibit glucosylceramide (GlcCer) formation by inhibiting the enzyme GlcCer synthase, thereby lowering the level of glycosphingolipids.) The isomers most active have the R,R-(D-threo)-configuration. Four enantiomers are produced during the synthesis. Because only the D-threo enantiomers are active in inhibiting the glucosylceramide synthase, resolution of the active D-threo inhibitors was performed by chiral chromatography.

Moreover, D-threo-PDMP has antitumor activity via inhibition of glycosphingolipid biosynthesis as described by Inokuchi J., *Cancer Letters* 38(1-2), 23-30, 1987.

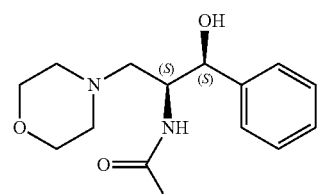

L-threo-PDMP

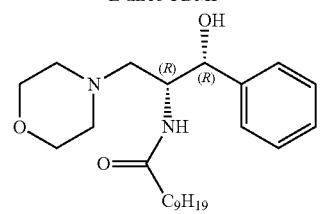

D-threo-PDMP

Furthermore, it was also reported that D-threo-PDMP suppresses synaptic function by Mizutani A. et al., *Biochem. Biophys. Res. Commun.*, 222, 494-498, 1996.

Preparation of enantiomerically pure D-threo-PDMP has been reported by Mitchell, Scott A. [*J. Org. Chem.*, 63 (24), 8837-8842, 1998]; Miura, T. et al, [*Bioorg. Med. Chem.*, 6, 1481-1498, 1998]; Shin, S. et al., [*Tetrahedron asymmetry*, 11, 3293-3301, 2000]; WO 2002012185

L-threo-PDMP is an agent for treating neuronal diseases WO 95/05177. This compound is also described to be an agent for protecting brain in U.S. Pat. No. 6,407,064. Moreover treatment with L-threo-PDMP after transient forebrain ischemia in rats ameliorated the deficit of a well learned spatial memory by an 8-arm maze task, suggesting a potential for neurodegenerative disorders as described by Inokuchi et al., *Ann. N.Y. Acad. Sci.*, 845(1), 219-224, 1998 and JP 10324671 (Seikagaku Kogyo Co.).

A stereoselective synthesis of enantiomerically pure D-threo-PDMP has also been described by Shin, S. et al., *Tetrahedron asymmetry*, 11, 3293-3301, 2000 and WO 2002012185 the key step is the regioselective cleavage by nitrogen nucleophiles, as morpholine, of the C(3)-N-bond of non-activated enantiomerically pure aziridine-2-methanols.

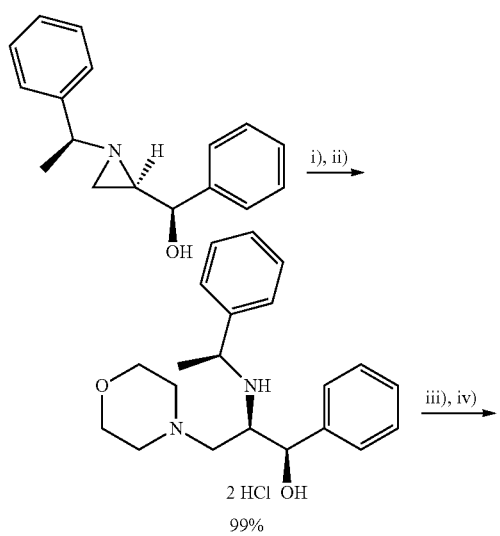

-continued

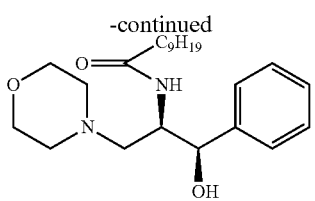

D-threo-PDMP 81% i) TMS-I, CH₃CN ii) a) morpholine b) HCl iii) Pd(OH)₂, H₂, AcOH, MeOH, 40° C. iv) 10% NaOH, decanoyl chloride 81%

On the other hand, the synthesis of enantiomerically pure (1S,2S)-1-phenyl-2-decanoylamino-3-morpholino-1-propanol (L-threo-PDMP) from L-serine has also been described by Mitchell, Scott A., *J. Org. Chem.*, 63 (24), 8837-8842, 1998.

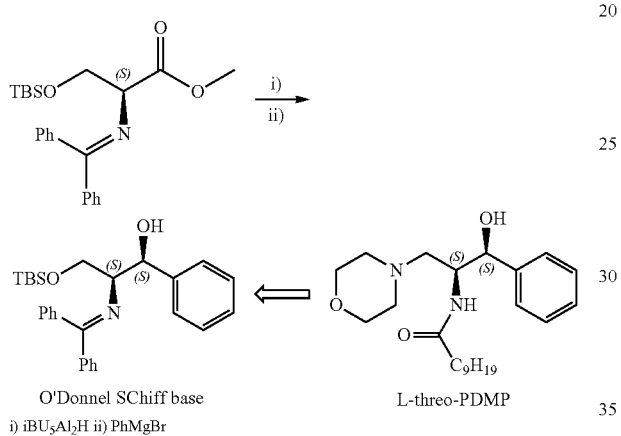

O'Donnel SChiff base     L-threo-PDMP i) iBU₅Al₂H ii) PhMgBr

Other known methods to obtain L-threo-PDMP are described by Miura, T. et al, *Bioorg. Med. Chem.*, 6, 1481-1498, 1998 and in JP-A-9-216858.

L-threo-PDMP is an agent for treating neuronal diseases WO 95/05177. This compound is also described to be an agent for protecting brain in U.S. Pat. No. 6,407,064. Moreover treatment with L-threo-PDMP after transient forebrain ischemia in rats ameliorated the deficit of a well learned spatial memory by an 8-arm maze task, suggesting a potential for neurodegenerative disorders as described by Inokuchi et al., *Ann. N.Y. Acad. Sci.*, 845(1), 219-224, 1998 and JP 10324671 (Seikagaku Kogyo Co.).

Synthesis of (1S,2S)-threo- and (1R,2S)-erythro-1-phenyl-2-palmitoylamino-3-N-morpholino-1-propanol (PPMP) were described starting from Garner aldehyde of L-serine, by Nishida, A., *Synlett*, 4, 389-390, 1998.

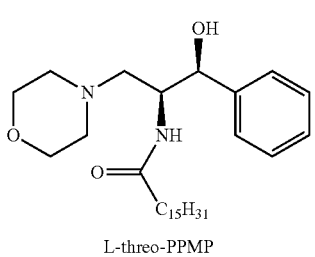

L-threo-PPMP

-continued

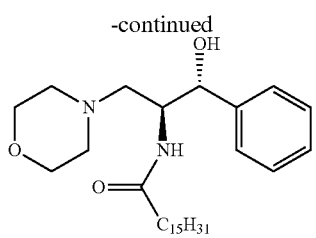

D-erythro-PPMP

Compounds with longer chain fatty acyl groups (than decanoyl) have been found to be substancially more effective as inhibitor of GCS. D-threo-1-phenyl-2-palmitoylamino-3-pyrrolidino-1-propanol (P4 or PPPP) analogues were first obtained by a Mannich reaction as described Abe, A. et al., *J. Biochem.*, 111, 191-196, 1992 or U.S. Pat. No. 5,916,911 and WO 2001004108.

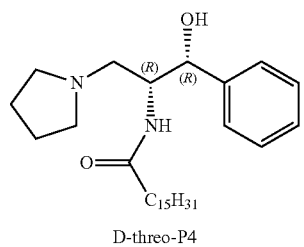

D-threo-P4

Preparation of D-threo-4'-hydroxy-P4, one of the most potent inhibitor of GCS, was described by Lee, L. et al., *J. Biol. Chem.*, 274, 21, 14662-14669, 1999. In addition, a series of dioxane substitutions was designed and tested. These included 3',4'-methylenedioxyphenyl-3',4'-ethylenedioxyphenyl-, and 3',4'-trimethylenedioxyphenyl-substituted homologues.

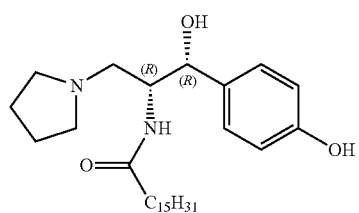

D-threo-4'-hydroxy-P4

Synthesis of enantiomerically pure D-threo-1-phenyl-2-benzyloxycarbonylamino-3-pyrrolidino-1-propanol (PBPP) and D-threo-P4 and its analogues from N-benzyloxycarbonyl-D-serine, was described by Jimbo M. et al, *J. Biochem.*, 127(3), 485-91, 2000 and EP 782992 (Seikagaku Kogyo Co.). PBPP is described as a potent GCS inhibitor.

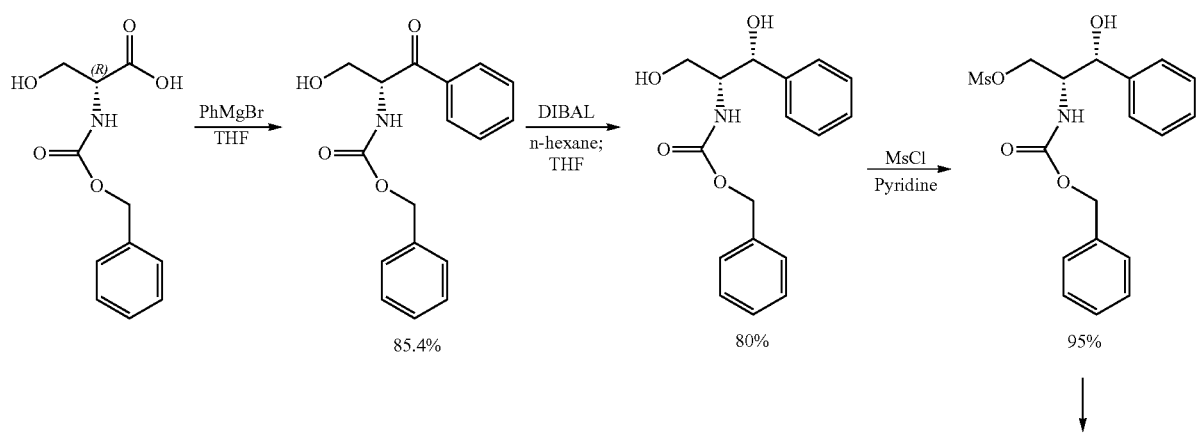
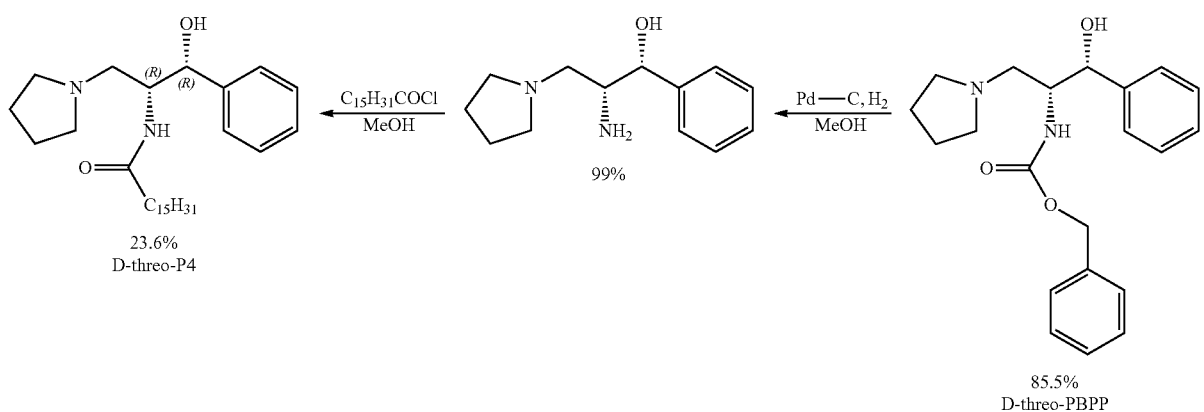
Novel prodrugs of P4 derivatives were described in US 20020198240 and WO 2002062777.
Synthesis of enantiomerically pure of D-threo-ethylenedioxy-P4 and D-threo-p-methoxy-P4 were described by Husain A. and Ganem B., *Tetrahedron Lett.*, 43, 8621-8623, 2002. The key step is a highly syn-selective additions of aryl Grignard reagents to Garner aldehyde.
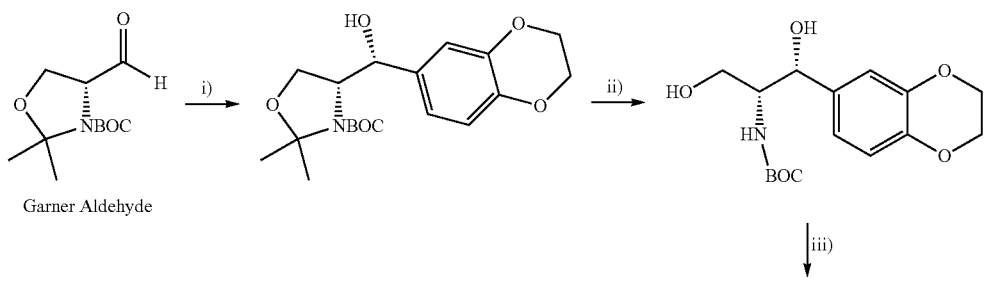

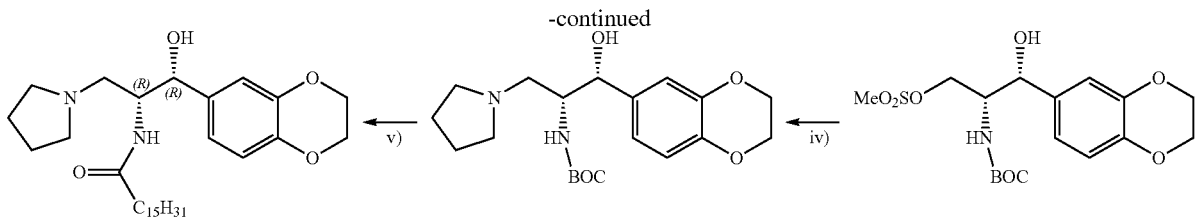

D-threo-ethylenedioxy-P4 i) 3,4-ethylenedioxyphenylmagnesium bromide, -78° C., CuI, THF; Me₂S, 64% ii) 0.1 N HCl, THF 82%, MsCl, Et₃N, DCM, 0° C., 85% iii) pyrrolidine, DMF, 45° C., 58% iv) 3 N HCl, 0° C., to RT then C₁₅H₃₁COCl, Et₃N, DMAP, DCM, -20° C., 87%

Diastereoselective synthesis of P4 analogues were described in US03/0153768 and WO 2003045928 (Genzyme Corp.); Oxazolines I [R1=(un)substituted aryl; R², R³=H, (un)substituted aliphatic; NR²R³=heterocyclic] are prepared as intermediates for P4 glucosyltransferase inhibitors from R¹CHO and R²R³NCOCH₂CN. Thus, methyl isocyanoacetate CNCH₂CO₂Me was treated with pyrrolidine and the amide was treated with 1,4-benzodioxane-6-carboxaldehyde, followed by hydrolysis of the oxazoline using HCl in methanol, reduction of the keto group of amide II using LiAlH₄, and acylation with palmitoyl chloride to give D,L-threo-ethylenedioxy-P4 III.

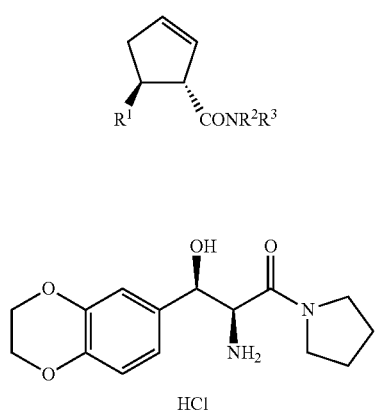

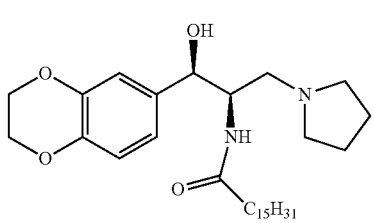

D,L-threo-3',4'-ethylenedioxy-P4

Synthesis of enantiopure P4 analogues were described in WO 2003008399 (Genzyme Corp.). P4 derivatives, such as I [R¹, R⁵=un(substituted) aromatic; R², R³=H, un(substituted) aliphatic; NR²R³=(un)substituted non-aromatic heterocyclic ring; R⁴=O, H₂], were prepared for their therapeutic use as GCS inhibitors. Thus, D-threo-ethylenedioxy-P4 was prepared via a multistep synthetic sequence starting from S-(+)-Ph glycinol, phenyl-α-bromoacetate, 1,4-benzodioxan-6-carboxaldehyde, pyrrolidine and palmitoyl chloride.

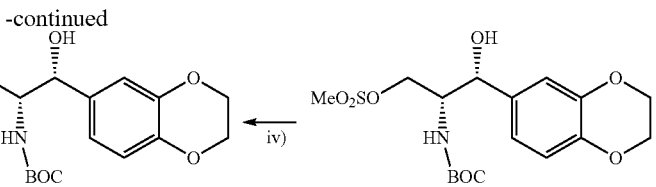

D-threo-3',4'-ethylenedioxy-P4

New D-threo-P4 analogues that bear ether substituents on the aromatic ring have been recently synthesized from D-serine and found to suppress neurite extension in an embryonic insect cell line as described by Slavish., J. P. et al., Bioorg. Med. Chem. Lett., 14, 1487-1490, 2004.

Further references which serve as background to the present invention are U.S. Pat. Nos. 5,945,442; 5,952,370; 6,030,995 and 6,051,598; Journal of Labelled Compounds & Radiopharmaceuticals (1996), 38(3), 285-97; Published PCT application WO 01/38228; and Kastron et al. Latvijas PSR Zinatnu Akademijas Vestis, Kimijas Serija (1965) (4), 474-7.

SUMMARY OF THE INVENTION

The present invention is directed to methods of using the compounds shown below as analgesics by administering to a mammal, in need of such administration a pharmaceutical composition containing one or more of the compounds or their pharmaceutically acceptable salts.

The present invention is still further directed to pharmaceutical compositions containing the compounds shown below and all other pharmaceutically acceptable salts of these compounds, to be used as analgesics.

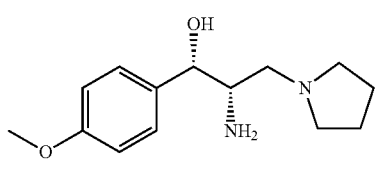
DL-threo
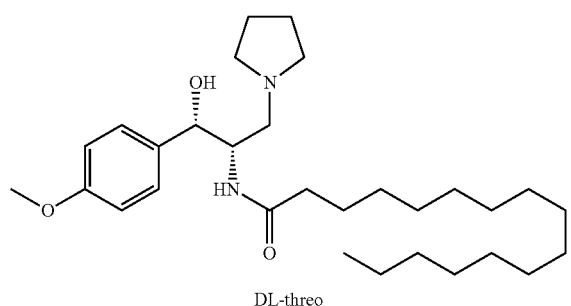
DL-threo
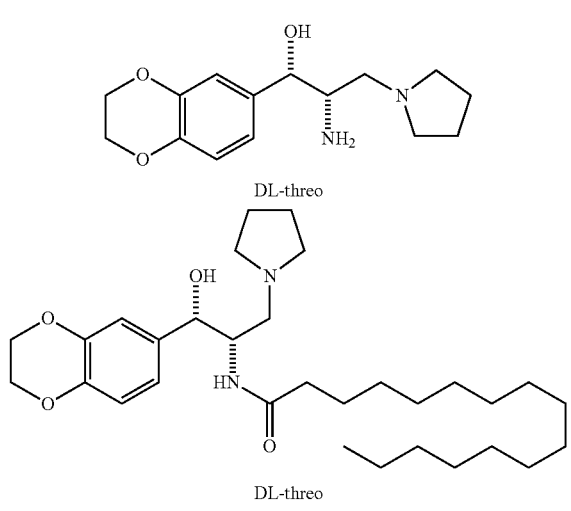
DL-threo
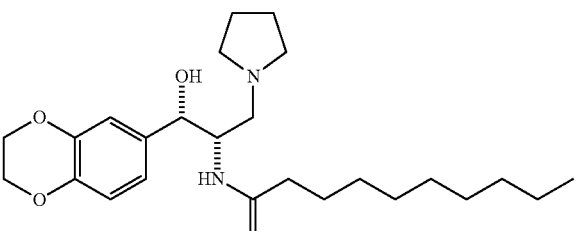
DL-threo
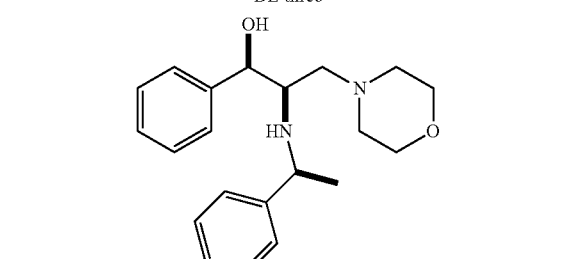
2 HCl
DL-threo
-continued
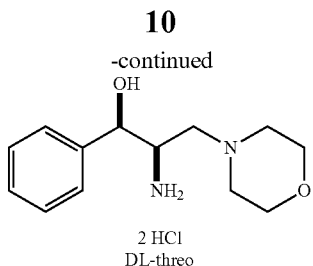
2 HCl
DL-threo
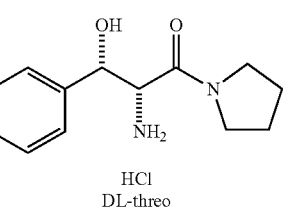
HCl
DL-threo
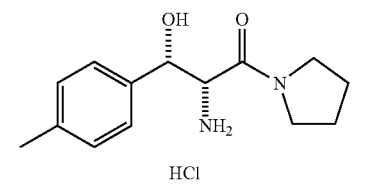
HCl
DL-threo
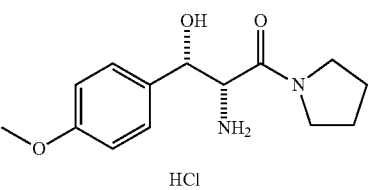
HCl
DL-threo
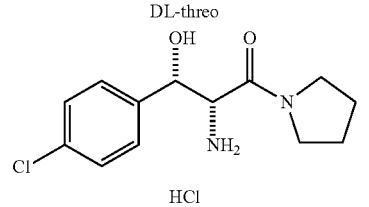
HCl
DL-threo
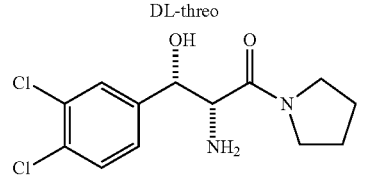
HCl
DL-threo
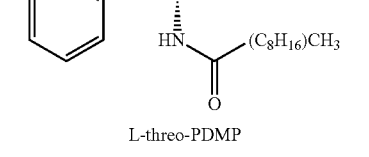
L-threo-PDMP

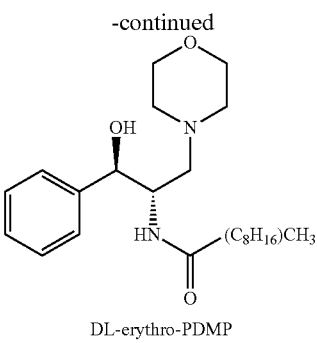

DL-erythro-PDMP

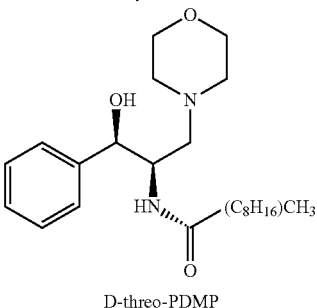

D-threo-PDMP

All of the above noted compounds have been described in the prior art literature. However, as far as the present inventors are aware their use as analgesics has not been discovered or known in the prior art.

DETAILED DESCRIPTION OF THE INVENTION

The chemical structures of the compounds used in the methods and compositions of the present invention are provided in the Summary Section of the present application for patent. All of compounds used in the methods and compositions of the present invention have two asymmetric carbons adjacent to one another and therefore, generally speaking, can exist in erythro or threo form, with each of these two forms having dextrorotatory (D) or levorotary (L) enantiomers. Nevertheless, most compounds presently used in the methods and compositions of the present invention are in the threo form which itself can have dextrorotatory (D) or levorotary (L) enantiomers. The scope of the present invention includes use of the threo and erythro isomers, mixtures of erythro and threo isomers, both enantiomers of the isomers in optically pure form, racemic mixtures and mixtures where the enantiomers are not present in equal amounts. In light of the foregoing, it should be clearly understood that the designation "DL" or "(+/−)" or "(±)" in this application includes the pure dextrorotatory enantiomer, the pure levorotatory enantiomer and all racemic mixtures, including mixtures where the two enantiomers are present in equal or in unequal proportions. Moreover, for simplicity sake in many of the structural formulas, such as in the example below, only one of the enantiomers is actually shown but when the designation "DL" (or "(+/−)" or "(±)") appears it also includes the enantiomeric form (mirror image) of the structure actually shown in the formula.

For Example:

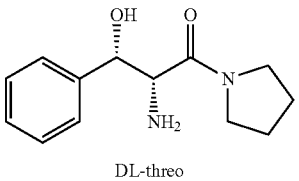 [SMILES: N[C@@H](C(=O)N1CCCC1)[C@@H](O)c1ccccc1]

DL-threo

In the example above, only one enantiomer is shown, but because the designation "DL" (or "(+/−)" or "(±)") appears below the formula, its optical isomer

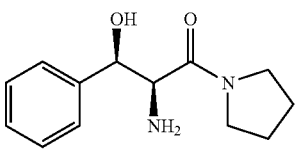

DL-threo and all racemic mixtures of the two optical isomers are also included.

Keeping the foregoing example in mind a person of ordinary skill in the art should readily understand the scope of each described example, although in a broad sense all enantiomers and racemic mixtures are within the scope of the invention.

Generally speaking the compounds used in the methods or compositions of the present invention may already be shown as hydrochloride salts. However, the compounds may also exist in salt free form or may form salts with pharmaceutically acceptable acids, other than hydrochloric acid, and such pharmaceutically acceptable salts are also within the scope of the invention.

The compounds used in the method or compositions of the invention have analgesic activity in mammals.

An art-accepted model or assay for measuring an analgesic effect of a compound in chronic pain (in particular peripheral neuropathy) is the model known as Kim and Chung 1992, Pain 150, pp 355-363 (Chung model). This model involves the surgical ligation of the L5 (and optionally the L6) spinal nerves on one side in experimental animals. Rats recovering from the surgery gain weight and display a level of general activity similar to that of normal rats. However, these rats develop abnormalities of the foot, wherein the hindpaw is moderately everted and the toes are held together. More importantly, the hindpaw on the side affected by the surgery appears to become sensitive to low-threshold mechanical stimuli and will perceive pain instead of the faint sensation of touch. This sensitivity to normally non-painful touch, called "tactile allodynia", develops within the first week after surgery and lasts for at least two months. The allodynia response includes lifting the affected hindpaw to escape from the stimulus, licking the paw and holding it in the air for many seconds. None of these responses is normally seen in the control group.

To produce the tactile allodynia, rats are anesthetized before surgery. The surgical site is shaved and prepared either with betadine or Novacaine. Incision is made from the thoracic vertebra Xlll down toward the sacrum. Muscle tissue is separated from the spinal vertebra (left side) at the L4-S2 levels. The L6 vertebra is located and the transverse process is carefully removed with a small rongeur to expose the L4-L6 spinal nerves. The L5 and L6 spinal nerves are isolated and tightly ligated with 6-0 silk thread. The same procedure is done on the right side as a control, except no ligation of the spinal nerves is performed.

After a complete hemostasis is confirmed, the wounds are sutured. A small amount of antibiotic ointment is applied to the incised area, and the rat is transferred to the recovery plastic cage under a regulated heat-temperature lamp.

On the day of the experiment, at least seven days after the surgery, typically six rats per test group are administered the test drugs by intraperitoneal (i.p.) injection or oral gavage (p.o.). For i.p. administration, the compounds are formulated in $H_2O$ and given in a volume of 1 ml/kg body weight by injecting into the intraperitoneal cavity. For p.o. administration, the compounds are formulated in $H_2O$ and given in a volume of 1 ml/kg body weight using an 18-gauge, 3 inch gavage needle that is slowly inserted through the esophagus into the stomach.

Tactile allodynia is assessed via von Frey hairs, which are a series of fine hairs with incremental differences in stiffness. Rats are placed in a plastic cage with a wire mesh bottom and allowed to acclimate for approximately 30 minutes. To establish the pre-drug baseline, the von Frey hairs are applied perpendicularly through the mesh to the mid-plantar region of the rats' hindpaw with sufficient force to cause slight buckling and held for 6-8 seconds. The applied force has been calculated to range from 0.41 to 15.1 grams. If the paw is sharply withdrawn, it is considered a positive response. A normal animal will not respond to stimuli in this range, but a surgically ligated paw will be withdrawn in response to a 1-2 gram hair. The 50% paw withdrawal threshold is determined using the method of Dixon, W. J., *Ann. Rev. Pharmacol. Toxicol.* 20:441-462 (1980) hereby incorporated by reference. Tactile allodynia is measured prior to and 15, 30, and 60 minutes after drug administration. The post-drug threshold is compared to the pre-drug threshold and the percent reversal of tactile sensitivity is calculated based on a normal threshold of 15.1 grams.

Table 1 below indicates the degree of pain reversal obtained in the Chung model with exemplary compounds used in accordance with the invention. The intraperitonial (i.p.) and/or intravenous (iv) administration of the compounds was in doses ranging from 1 µg/kg to 300 µg/kg or 3 mg/kg PO and the peak percentage of reversal of allodynia was measured at 15, 30 or 60 minutes after administration, as is indicated in the table. Data are expressed as the highest % allodynia reversal (out of 3 time points: 15 min, 30 min, or 60 min. post-drug) with a minimum of a 20% allodynia reversal in the rat Chung model. Comparisons between groups (drug treated vs. saline treated) were made using a two-tailed, 2-sample, unpaired t-test. Compounds that are not shown which were not statistically analgesic following an IP dose of 300 ug/kg, but may still be analgesic. Compounds that do not exhibit significant analgesia at 100 mg/kg are not considered to be analgesic.

TABLE 1

| Compound # | Chemical Formula | Peak % Pain reversal: time post dose | Dose µg/kg, Mode of administ. |
|---|---|---|---|
| 9 | (structure) DL-threo | 88% 60 min | 30 µg/kg IP |
| 6 | (structure) DL-threo | 92% 60 min | 30 µg/kg IP |
| 2 | (structure) 2·HCl L-threo | 91% 60 min | 100 µg/kg IP |

TABLE 1-continued

| Compound # | Chemical Formula | Peak % Pain reversal: time post dose | Dose μg/kg, Mode of administ. |
|---|---|---|---|
| 1:1 Racemic mixture of 2 and 4 | 2•HCl L-threo (phenyl-CH(OH)-CH(NH2)-CH2-morpholine) and 2•HCl D-threo (phenyl-CH(OH)-CH(NH2)-CH2-morpholine) | 87% 30 min | 30 μg/kg IP |
| 5 | 2•HCl; phenyl-CH(OH)-CH(NH-CH(CH3)-phenyl)-CH2-morpholine, D-threo | 85% 60 min | 300 μg/kg IP |
| 7 | benzodioxane-CH(OH)-CH(NH-C(O)-(CH2)10CH3)-CH2-pyrrolidine, DL-threo | 26% 30 min | 1 μg/kg IP |
| 16 | phenyl-CH(OH)-CH(NH2)-C(O)-pyrrolidine, HCl, DL-threo | 93% 60 min | 300 μg/kg IP |

TABLE 1-continued

| Compound # | Chemical Formula | Peak % Pain reversal: time post dose | Dose μg/kg, Mode of administ. |
|---|---|---|---|
| 17 | 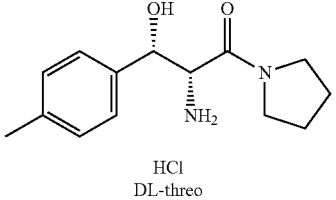 [SMILES: Cc1ccc([C@H](O)[C@@H](N)C(=O)N2CCCC2)cc1]<br>HCl<br>DL-threo | 100%<br>60 min | 300 μg/kg IP |
| 15 | 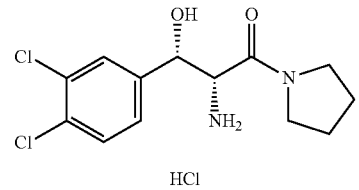<br>HCl<br>DL-threo | 42%<br>60 min | 300 μg/kg IP |
| L-threo-PDMP<br>Available from Matreya, LLC | 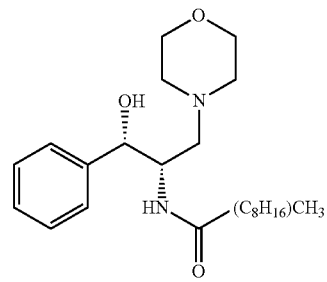<br>L-threo-PDMP | 100%<br>30 min | 30 μg/kg PO |
| DL-erythro-PDMP<br>Available from Matreya, LLC | 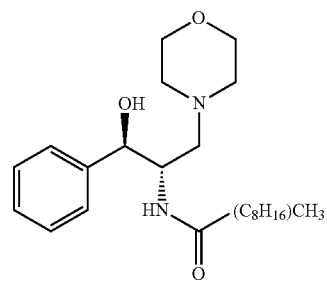<br>DL-erythro-PDMP | 68%<br>30 min | 1000 μg/kg IP |
| D-threo-PDMP<br>Available from Matreya, LLC | 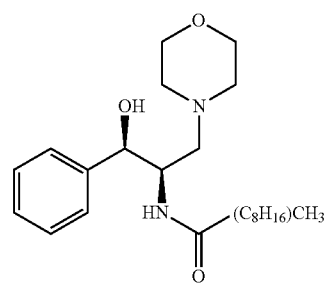<br>D-threo-PDMP | 77%<br>60 min | 1000 μg/kg IP |

Modes of Administration:

The compounds used in the methods and compositions of the invention are administered at pharmaceutically effective dosages. Such dosages are normally the minimum dose necessary to achieve the desired therapeutic effect; in the treatment of chromic pain, this amount would be roughly that necessary to reduce the discomfort caused by the pain to tolerable levels. For human adults such doses generally will be in the range 0.1-5000 mg/day; more preferably in the range 1 to 3000 mg/day, still more preferably in the range of 10 mg to 1000 mg/day. However, the actual amount of the compound to be administered in any given case will be determined by a physician taking into account the relevant circumstances, such as the severity of the pain, the age and weight of the patient, the patient's general physical condition, the cause of the pain, and the route of administration.

Preferably, the patient will be given the compound in a composition orally in any pharmaceutically acceptable form, such as a tablet, liquid, capsule, powder and the like. However, other routes may be desirable or necessary, particularly if the patient suffers from nausea. Such other routes may include, without exception, transdermal, intraperitonial, parenteral, subcutaneous, intranasal, intrathecal, intramuscular, intravenous and intrarectal modes of delivery and the present invention extends to pharmaceutical compositions adapted for such deliveries. Pharmaceutical compositions tend to contain a pharmaceutically acceptable excipient. Such excipient are well known in the art and may be a carrier or a diluent; this is usually mixed with the active compound, or permitted to dilute or enclose the active compound. If a diluent, the carrier may be solid, semi-solid, or liquid material that acts as an excipient or vehicle for the active compound. The formulations of the compositions may also include wetting agents, emulsifying agents, preserving agents, sweetening agents, and/or flavoring agents. If used as in an ophthalmic or infusion format, the formulation will usually contain one or more salt to influence the osmotic pressure of the formulation.

METHODS FOR OBTAINING THE COMPOUNDS OF THE INVENTION, EXPERIMENTAL

The compound used in the methods of treatment and pharmaceutical compositions of the invention are per se known in the art and can be obtained from commercial sources or by the synthetic processes described in the pertinent references (primarily in Shin, S. et al., [*Tetrahedron asymmetry*, 11, 3293-3301, 2000] and US 20030153768) and noted in the Background Art section of the present application. For the purposes of the present invention the majority of the compounds were nevertheless synthesized and their preparations are described below.

General $^1$H NMR spectra were recorded at ambient temperature with an Avance 300 (Bruker) spectrometer. The compounds were analyzed by reverse phase high performance liquid chromatography (HPLC) using a Waters Autopurification System equipped with a Waters 2525 Pump, a Waters 2696 photodiode array detector, and a XTerra column (Part. No. 186000482, 5 μm, C18, 4.5×50 mm).

The HPLC method used was a gradient of 5% solvent B to 100% in 7 min. Solvent A was $H_2O$ with 0.05% TFA and solvent B was $CH_3CN$ with 0.05% TFA (Method A).

Melting points were measured with a Büchi B-545 melting point apparatus and were uncorrected. To isolate reaction products the solvent were removed by evaporation using a vacuum rotatory evaporator, the water bath temperature not exceeding 40° C.

Preparation of Compound 6, Compound 7, Compound 8 and Compound 9

2-Isocyano-1-(pyrrolidin-1-yl)ethanone BLE 04098

To stirred and cooled (0° C.) methyl isocyanoacetate (96% technical grade, 5.0 g, 47.8 mmol) was slowly added in 0.75 h pyrrolidine (6.5 mL, 78 mmol). The mixture was stirred for 1.5 h with continued cooling and then concentrated. The resulting oil was co-evaporated twice from $CH_2Cl_2$:hexane to remove residual pyrrolidine. 2-Isocyano-1-(pyrrolidin-1-yl) ethanone BLE 04098 was obtained as a yellow solid (6.85 g, 98% yield) and used in the next step without purification.

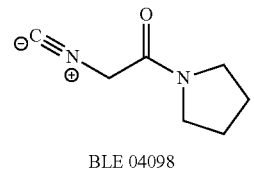

BLE 04098

MW: 138.17; Yield: 98%; yellow solid; Mp (° C.)=73.9.
$^1$H-NMR (CDCl$_3$): 1.81-2.08 (m, 4H, 2×CH$_2$), 3.35-3.45 (m, 2H, —NCH$_2$), 3.50-3.60 (m, 2H, —NCH$_2$), 4.23 (s, 2H, CH$_2$CO).

trans-(4,5-Dihydro-5-(2,3-dihydrobenzo[b][1,4]dioxin-6-yl)oxazol-4-yl)(pyrrolidin-1-yl)methanone BLE 04100

To a stirred and cooled (0° C.) solution of potassium hydroxide (0.43 mg, 7.60 mmol) in MeOH (6.5 mL) were added successively 1,4-benzodioxan-6-carboxaldehyde (1.31 g, 7.96 mmol) and 2-isocyano-1-(pyrrolidin-1-yl)ethanone BLE 04098 (1.0 g, 6.57 mmol). The solution was stirred 3 h at 0° C. and then concentrated. The residue was partitioned between EtOAc (100 mL) and water. The organic layer was combined with 2 additional EtOAc extracts (2×100 mL), washed with brine, dried over MgSO$_4$, filtered and evaporated. Concentration afford to a crude product which was purified by column chromatography on silica (EtOAc) to yield, after evaporation and drying, to trans-4,5-dihydro-5-(2,3-dihydrobenzo[b][1,4]dioxin-6-yl)oxazol-4-yl)(pyrrolidin-1-yl)methanone BLE 04100 as a colourless oil (1.76 g, 89% yield).

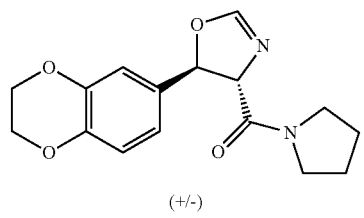

(+/-)

BLE 04100

MW: 440.49; Yield: 89%; colourless oil.
$^1$H-NMR (CDCl$_3$): 1.75-2.10 (m, 4H, 2×CH$_2$), 3.40-3.59 (m, 6H, 3×CH$_2$N), 3.85-4.00 (m, 1H, CHN), 4.26 (s, 4H, CH₂O), 4.59 (dd, 1H, J=7.5 Hz, J=2.2 Hz, CH—N), 6.00 (d, 1H, J=7.5 Hz, CH—O), 6.75-6.90 (m, 3H, ArH), 7.00 (d, 1H, J=2.2 Hz, CH=N).

trans-(4,5-Dihydro-5-(4-methoxyphenyl)oxazol-4-yl) (pyrrolidin-1-yl)methanone SLA 07074

To a stirred and cooled (0° C.) solution of potassium hydroxide (0.37 g, 6.57 mmol) in methanol (30 mL) was added a mixture of 4-methoxy-benzaldehyde (0.88 mL, 7.23 mmol) and 2-isocyano-1-(pyrrolidin-1-yl)ethanone BLE 04098 (1.0 g, 6.57 mmol). The solution was stirred 4 h with continued cooling and then concentrated. The residue was partitioned between ethyl acetate and water. The organic layer was combined with additional ethyl acetate extracts, washed with aqueous sodium chloride and dried over MgSO₄. Concentration afforded a crude product as a glassy solid. Flash chromatography over silica (ethyl acetate) yielded to trans-(4,5-dihydro-5-(4-methoxyphenyl)oxazol-4-yl)(pyrrolidin-1-yl)methanone SLA 07074 as a pale yellow solid (1.2 g, 90.5%).

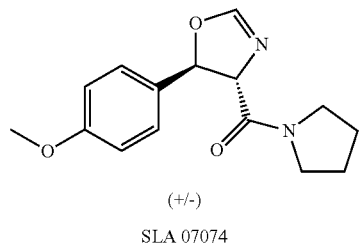 [SMILES: COc1ccc([C@H]2OC=N[C@@H]2C(=O)N2CCCC2)cc1]

(+/-)
SLA 07074

MW: 274.32; Yield: 90.5%; pale yellow solid; Mp (° C.): 91.2.

R$_f$: 0.30 (EtOAc).

¹H-NMR (CDCl₃): 1.75-2.08 (m, 4H, 2×CH₂), 3.40-3.58 (m, 3H, CH₂N), 3.52 (s, 3H, CH₃O), 3.88-3.98 (m, 1H, CH₂N), 4.59 (dd, 1H, J=7.6 Hz, J=2.2 Hz, CH—N), 6.06 (d, 1H, J=7.6 Hz, CH—O), 6.90 (d, 2H, J=8.7 Hz, ArH), 7.01 (d, 1H, J=2.2 Hz, CH=N), 7.25 (d, 2H, J=8.7 Hz, ArH).

MS-ESI m/z (% rel. Int.): 275.1 ([MH]⁺, 10), 247.1 (100).

HPLC: Method A, detection UV 280 nm, SLA 07074 RT=5.2 min, peak area 92%.

DL-threo-2-Amino-3-hydroxy-3-(4-methoxyphenyl)-1-(pyrrolidin-1-yl)propan-1-one hydrochloride SLA 07078

To a stirred solution of trans-(4,5-dihydro-5-(4-methoxyphenyl)oxazol-4-yl)(pyrrolidin-1-yl)methanone SLA 07074 (1.61 g, 5.93 mmol) in methanol (13 mL) was added hydrochloric acid (1 mL). After heating at 50° C. for 3 h the mixture reaction was concentrated and the resulting yellow oil was co-evaporated twice with ethyl acetate before solidifying. Trituration (ethyl acetate) and drying afforded DL-threo-2-amino-3-hydroxy-3-(4-methoxyphenyl)-1-(pyrrolidin-1-yl)propan-1-one hydrochloride SLA 07078 as a white solid (1.64 g, 93%).

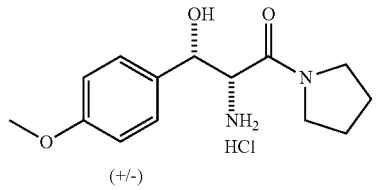

(+/-)
SLA 07078

MW: 300.78; Yield: 93%; white Solid; Mp (° C.): 177.0.

¹H-NMR (CD₃OD,.): 1.32-1.50 (m, 1H, CH₂), 1.50-1.88 (m, 3H, CH₂), 2.15-2.28 (m, 1H, CH₂N), 3.15-3.42 (m, 4H, 2×CH₂N), 3.79 (s, 3H, CH₃O), 4.06 (d, 1H, J=9.2 Hz, CH—N), 4.78 (d, 1H, J=9.2 Hz, CHO), 6.94 (d, 2H, J=8.5 Hz, ArH), 7.34 (d, 2H, J=8.5 Hz, ArH).

¹³C-NMR (CD₃OD,.): 24.8, 26.6, 47.2, 47.6, 55.9, 59.6, 73.9, 115.0 (2×C), 128.9 (2×C), 132.5, 161.7, 166.4.

DL-threo-2-amino-3-(2,3-dihydrobenzo[b][1,4]dioxin-6-yl)-3-hydroxy-1-(pyrrolidin-1-yl)propan-1-one hydrochloride Compound 12

To a stirred solution of trans-4,5-dihydro-5-(2,3-dihydrobenzo[b][1,4]dioxin-6-yl)oxazol-4-yl)(pyrrolidin-1-yl) methanone BLE 04100 (1.74 g, 5.77 mmol) in methanol (15 mL) was added hydrochloric acid (1 mL). After heating at 50° C. for 3 h the mixture reaction was concentrated and the resulting yellow oil was co-evaporated twice with ethyl acetate before solidifying. Trituration (ethyl acetate) and drying afforded DL-threo-2-amino-3-(2,3-dihydrobenzo[b][1,4] dioxin-6-yl)-3-hydroxy-1-(pyrrolidin-1-yl)propan-1-one hydrochloride Compound 12 as a white solid (1.85 g, 95%).

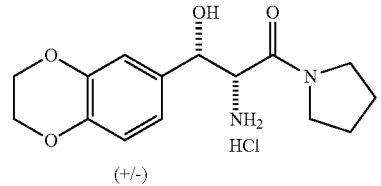

Compound 12

(+/-)

MW: 328.79; Yield: 95.0%; White Solid; Mp (° C.): 176.2.

¹H-NMR (CD₃OD,.): 1.42-1.58 (m, 1H, CH₂), 1.58-1.70 (m, 1H, CH₂), 1.70-1.88 (m, 2H, CH₂), 3.20-3.45 (m, 4H, N—CH₂), 4.06 (d, 1H, J=9.1 Hz, CH—N), 4.25 (s, 2H, CH₂), 4.75 (d, 1H, J=9.2 Hz, CH—O), 4.89 (s, 2H, CH₂), 6.82-6.95 (m, 3H, ArH).

¹³C-NMR (CD₃OD,.): 24.9, 26.7, 47.3, 47.6, 59.5, 65.7, 73.6, 116.4, 118.3, 120.3, 133.7, 145.1, 145.6, 166.4.

DL-threo-2-Amino-1-(2,3-dihydrobenzo[b][1,4]dioxin-6-yl)-3-(pyrrolidin-1-yl)propan-1-ol Compound 6.

To a stirred suspension of trans-(4,5-dihydro-5-(4-methoxyphenyl)oxazol-4-yl)(pyrrolidin-1-yl)methanone SLA 07074 (1.79 g, 5.44 mmol) in THF (220 mL) was slowly added at 0° C., in two portions, LiAlH₄ (1.28 g, 33.7 mmol). The mixture was stirred at RT for 3.5 h and quenched by a slow addition of water at 0° C. (350 mL). The white suspension was concentrated to remove THF and taken back in a mixture of CH₂Cl₂ (300 mL) and 1 N aqueous HCl (50 mL).

The aqueous layer was basified to pH=10-11 by slow addition of 1 N aqueous NaOH. The organic layer was removed; two more extracts were combined and dried over MgSO$_4$, filtered and evaporated. Concentration afforded to a crude product as a yellow oil. This material was purified by column chromatography on silica (CH$_2$Cl$_2$:MeOH:NH$_4$OH 20%=94:5:1) to led to DL-threo-2-amino-1-(2,3-dihydrobenzo[b][1,4]dioxin-6-yl)-3-(pyrrolidin-1-yl)propan-1-ol Compound 6 (0.705 g, 46.5% yield) as a near colorless gum.

Compound 6

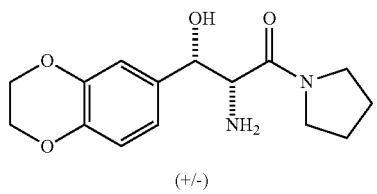

(+/-)

MW: 278.35; Yield: 46.5%; Colorless Gum.
R$_f$: 0.20 (CH$_2$Cl$_2$:MeOH:NH$_4$OH 20%=94:5:1).
$^1$H-NMR (CDCl$_3$): 1.70-1.85 (m, 4H, 2×CH$_2$), 2.40-2.70 (m, 6H, 3×CH$_2$N—), 3.05-3.15 (m, 1H, CH—N), 4.25 (s, 4H, CH$_2$O), 4.55 (d, 1H, J=2.2 Hz, CH—O), 5.30 (s, 1H, —OH), 6.75-6.90 (m, 3H, ArH).

N-(DL-threo-1-(2,3-dihydrobenzol[b][1,4]dioxin-6-yl)-1-hydroxy-3-(pyrrolidin-1-yl)propan-2-yl)decanamide Compound 7

To a stirred solution of DL-threo-2-amino-1-(2,3-dihydrobenzo[b][1,4]dioxin-6-yl)-3-(pyrrolidin-1-yl)propan-1-ol Compound 12 (0.186 g, 0.67 mmol) in 10 mL CH$_2$Cl$_2$ were added, in order, N-hydroxysuccinimide (0.081 g, 0.70 mmol) in 2 mL CH$_2$Cl$_2$, triethylamine (112 μL, 0.80 mmol) and decanoyl chloride (125 μL, 0.60 mmol). The mixture was stirred overnight at RT and then partitioned between CH$_2$Cl$_2$ and 1 N aqueous sodium hydroxide. The organic layer was dried over MgSO$_4$, filtered and evaporated and the residue obtained was purified by column chromatography on silica (CH$_2$Cl$_2$:MeOH=95:5). A white solid N-(DL-threo-1-(2,3-dihydrobenzo[b][1,4]dioxin-6-yl)-1-hydroxy-3-(pyrrolidin-1-yl)propan-2-yl)palmitamide Compound 7 was obtained (126 mg, 43.5% yield).

Compound 7

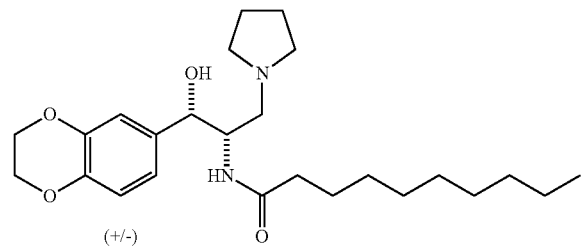

(+/-)

MW: 516.76; Yield: 43.5%; White Solid; Mp (° C.): 84.6.
R$_f$: 0.40 (MeOH:CH$_2$Cl$_2$=10:90).
$^1$H-NMR (CDCl$_3$): 0.88 (t, 3H, J=6.7 Hz, CH$_3$), 1.12-1.39 (m, 12H), 1.40-1.60 (m, 2H, CH$_2$), 1.72-1.90 (m, 4H, 2×CH$_2$), 2.10 (t, 2H, J=6.7 Hz, CH$_2$), 2.55-2.90 (m, 6H), 4.13-4.30 (m, 1H, CH—N), 4.24 (s, 4H, CH$_2$N), 4.91 (d, 1H, J=3.3 Hz, CH—O), 5.90 (d, 1H, J=7.4 Hz, NH), 6.75-6.88 (m, 3H, ArH), OH not seen.
$^{13}$C-NMR (CDCl$_3$): 14.1, 22.7, 23.6 (2×C), 25.6, 29.1, 29.3, 31.9, 36.8, 52.3, 55.1 (2×C), 57.7, 64.3 (2×C), 75.2, 77.2, 115.0, 117.0, 118.9, 134.4, 142.8, 143.4, 173.5, 174.8.
MS-ESI m/z (% rel. Int.): 433.1 ([MH]$^+$, 100).
HPLC: Method A, detection UV 280 nm, Compound 7, RT=5.2 min, peak area 96.2%.

N-(DL-threo-1-(2,3-Dihydrobenzol[b][1,4]dioxin-6-yl)-1-hydroxy-3-(pyrrolidin-1-yl)propan-2-yl)palmitamide Compound 8

To a stirred solution of DL-threo-2-amino-1-(2,3-dihydrobenzo[b][1,4]dioxin-6-yl)-3-(pyrrolidin-1-yl)propan-1-ol Compound 12 (0.158 g, 0.57 mmol) in 10 mL CH$_2$Cl$_2$ were added, in order, N-hydroxysuccinimide (0.068 g, 0.59 mmol) in 2 ml CH$_2$Cl$_2$, triethylamine (95 μL, 0.68 mmol) and palmitoyl chloride (155 μL, 0.511 mmol) in 3 mL CH$_2$Cl$_2$. The mixture was stirred overnight at RT and then partitioned between CH$_2$Cl$_2$ and 1 N aqueous sodium hydroxyde. The organic layer was purified by column chromatography on silica using as eluent CH$_2$Cl$_2$:MeOH=95:5. A white solid N-(DL-threo-1-(2,3-dihydrobenzo[b][1,4]dioxin-6-yl)-1-hydroxy-3-(pyrrolidin-1-yl)propan-2-yl)palmitamide Compound 8 was obtained (148 mg, 50.4% yield).

Compound 8

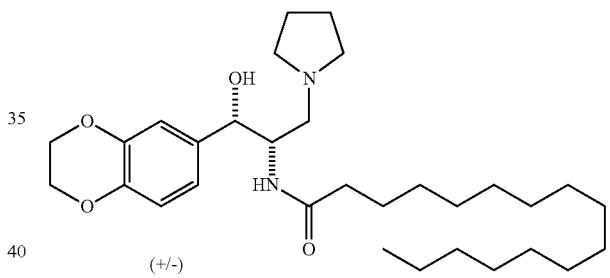

(+/-)

MW: 516.7; Yield: 50.4%; White Solid; Mp (° C.): 66.4.
R$_f$: 0.50 (MeOH:CH$_2$Cl$_2$=10:90).
$^1$H-NMR (CDCl$_3$): 0.88 (t, 3H, J=6.7 Hz, CH$_3$), 1.15-1.35 (m, 24H), 1.45-1.58 (m, 2H, CH$_2$), 1.75-1.90 (m, 4H, 2×CH$_2$), 2.10 (t, 2H, J=7.4 Hz, CH$_2$), 2.61 (s, 1H, OH), 2.52-2.72 (m, 4H), 2.72-2.92 (m, 2H), 4.15-4.22 (m, 1H, CH—N), 4.24 (s, 4H, CH$_2$N), 4.92 (d, 1H, J=3.3 Hz, CH—O), 6.08 (d, 1H, J=7.4 Hz, NH), 6.75-6.90 (m, 3H, ArH).
MS-ESI m/z (% rel. Int.): 517.2 ([MH]$^+$, 100).
HPLC: Method A, detection UV 280 nm, Compound 8 RT=6.60 min, peak area 97.2%.

DL-threo-2-Amino-1-(4-methoxyphenyl)-3-(pyrrolidin-1-yl)propan-1-ol Compound 9

To a stirred suspension of DL-threo-[5-(4-methoxy-phenyl)-4,5-dihydro-oxazol-4-yl]-pyrrolidin-1-yl-methanone SLA 07078 (1.61 g, 5.35 mmol) in tetrahydrofuran (200 mL) under nitrogen atmosphere was slowly added, in two portions, lithium aluminium hydride (1.22 g, 32.12 mmol) at 0° C. The mixture reaction was stirred at RT for 17 h, and then quenched by a slow, dropwise addition of water (50 mL). The white suspension was then concentrated to remove THF and taken back up in a mixture of 300 mL CH$_2$Cl$_2$ and 1N aqueous hydrochloric acid (50 mL). The aqueous layer was basified to pH=10-11 by a slow addition of 1N aqueous sodium hydroxyde. The organic layer was removed, combined with additional CH$_2$Cl$_2$ extracts (4×200 mL) and dried over MgSO$_4$, filtered and evaporated. The crude product was purified by column chromatography on silica (CH$_2$Cl$_2$:MeOH: NH$_3$=94:05:01). After evaporation and drying, DL-threo-2-amino-1-(4-methoxyphenyl)-3-(pyrrolidin-1-yl)propan-1-ol Compound 9 was obtained (0.62 g, 46%) as a pale yellow solid.

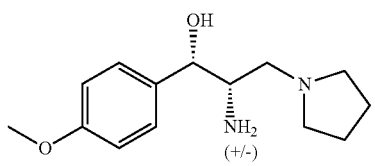

Compound 9

MW: 250.34; Yield: 46%; Pale Yellow Solid; Mp (° C.): 77.7.

R$_f$: 0.35 (CH$_2$Cl$_2$:MeOH:NH$_3$=94:05:01).

$^1$H-NMR (CDCl$_3$): 1.65-1.87 (s, 4H, 2×CH$_2$), 2.40-2.90 (m, 9H, CH$_2$N, NH$_2$ & OH), 3.11-3.17 (m, 1H, CH—N), 3.81 (s, 3H, CH$_3$O), 4.61 (d, 1H, J=3.8 Hz, CH—O), 7.89 (d, 2H, J=8.6 Hz, ArH), 7.26 (d, 2H, J=8.5 Hz, ArH).

$^{13}$C-NMR (CDCl$_3$): 23.6 (2×C), 54.5, 54.7 (2×C), 55.3, 60.1, 75.9, 113.6, 127.4, 134.4, 158.8.

MS-ESI m/z (% rel. Int.): 251.1 ([MH]$^+$, 100).

Preparation of Compound 2, 4 and 5

Benzyl (S)-3-hydroxy-1-oxo-1-phenylpropan-2-ylcarbamate TTA 08010B

To a stirred solution of Z-L-Ser-OH (6.00 g, 25.08 mmol) in 32 mL of anhydrous THF at 0° C. under nitrogen was added dropwise 1 M phenylmagnesium bromide in THF (32 mL, 200 mmol). The mixture was stirred 15 h at RT under nitrogen. A solution of 2 M HCl (100 mL) was slowly added at 0° C. and the mixture was partitioned between ethyl acetate (750 mL) and acidic water. The organic layer was washed with water (2×20 mL), 1 N aqueous sodium bicarbonate (2×20 mL), brine (2×20 mL) and dried over MgSO$_4$. After removing ethyl acetate by evaporation at 30-35° C., the crude product (4.50 g, 60% yield) was cristallized in a mixture of ethyl acetate:hexane=25 mL:20 mL to give benzyl (S)-3-hydroxy-1-oxo-1-phenylpropan-2-ylcarbamate TTA 08010B as a white solid (1.40 g, 20% yield).

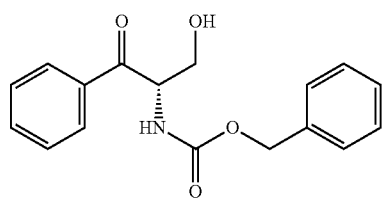

TTA 08010B

MW: 299.32; Yield: 20%; White Solid; Mp (° C.): 106.5.

R$_f$: 0.75 (CH$_2$Cl$_2$:MeOH=9:1).

$^1$H-NMR (CDCl$_3$): 2.78 (s, 1H, OH), 3.85-3.93 (m, 1H, CH$_2$O), 4.00-4.09 (m, 1H, CH$_2$O), 5.14 (s, 2H, ArCH$_2$O), 5.40 (t, 1H, J=3.3 Hz, CH), 6.17 (d, 1H, J=6.4 Hz, NH), 7.35 (s, 5H, ArH), 7.49 (t, 2H, J=7.60 Hz, ArH), 7.62 (t, 1H, J=7.1 Hz, ArH), 8.99 (t, 2H, J=7.6 Hz, ArH).

$^{13}$C-NMR (CDCl$_3$): 58.3, 64.6, 67.3, 128.1, 128.3, 128.6, 128.7, 129.0, 134.1, 136.0, 156.6, 196.6.

MS-ESI m/z (% rel. Int.): 300.1 ([MH]$^+$, 5), 256.1 (100).

HPLC: Method A, detection UV 254 nm, TTA 08010B RT=5.40 min, peak area 98.5%.

[ ]$^{22}_D$=−5.8 (c=1.00, MeOH).

Benzyl L-threo-1,3-dihydroxy-1-phenylpropan-2-ylcarbamate TTA 08012

To a stirred solution of benzyl (S)-3-hydroxy-1-oxo-1-phenylpropan-2-ylcarbamate TTA 08010B (1.40 g, 4.70 mmol) in 28 mL of anhydrous THF at −78° C. under nitrogen was added slowly dropwise 1 M DIBAL-H in hexane (18.8 mL, 18.80 mmol). The mixture was stirred 2 h at −78° C. then 1.5 h at RT. A solution of 2 M HCl (35 mL) was slowly added at −20° C. and the mixture was partitioned between ethyl acetate (750 mL) and acidic water. The organic phase was washed with water (2×20 mL), brine (2×20 mL) and dried over MgSO$_4$. After removing ethyl acetate by evaporation at 30-35° C., the crude product was purified by column chromatography on silica (CH$_2$Cl$_2$:MeOH=98:2 to 97:3) to give benzyl L-threo-1,3-dihydroxy-1-phenylpropan-2-ylcarbamate TTA 08012 as a white solid (1.10 g, 78% yield).

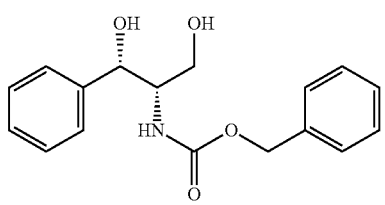

TTA 08012

MW: 301.34; Yield: 78%; White Solid; Mp (° C.): 102.5.

R$_f$: 0.30 (CH$_2$Cl$_2$:MeOH=95/5).

$^1$H-NMR (CDCl$_3$): 3.08 (t, 1H, J=5.0 Hz, OH), 3.59 (d, 1H, J=3.1 Hz, OH), 3.64-3.78 (m, 2H, CH$_2$O), 3.80-3.89 (m, 1H, CH), 4.95 (s, 2H, ArCH$_2$O), 5.57 (d, 1H, J=8.3 Hz, NH), 7.17-7.38 (m, 10H, ArH).

$^{13}$C-NMR (CDCl$_3$): 57.5, 63.6, 66.9, 73.8, 126.0, 127.8, 127.9, 128.1, 128.5, 128.6, 136.2, 141.0, 156.9.

MS-ESI m/z (% rel. Int.): 302.0 ([MH]$^+$, 5); 132.0 (100).

HPLC: Method A, detection UV 254 nm, TTA 08012 RT=5.00 min, peak area 99.5%.

[ ]$^{22}_D$=+39.4 (c=1.00, MeOH).

Benzyl L-threo-1-hydroxy-3-morpholino-1-phenyl-propan-2-ylcarbamate hydrochloride Compound 1

To a stirred solution of benzyl L-threo-1,3-dihydroxy-1-phenylpropan-2-ylcarbamate TTA 08012 (1.00 g, 3.30 mmol) in 13 mL of pyridine at −10° C. was added dropwise methanesulfonyl chloride (0.27 mL, 3.50 mmol). The mixture was stirred 6 h at 20° C. under nitrogen. Pyridine was removed by evaporation at 30-35° C. and the residue was partitioned between ethyl acetate (250 mL) and 0.1 N HCl (20 mL). The organic phase was washed with water (20 mL), brine (20 mL), dried over MgSO$_4$ and evaporated to give after drying L-threo-1-hydroxy-3-methanesulfonyl-1-phenylpropan-2-ylcarbamate TTA 08014 (1.25 g, 65% yield). To a stirred solution of crude benzyl L-threo-1-hydroxy-3-methanesulfonyl-1-phenylpropan-2-ylcarbamate TTA 08014 (1.25 g, 3.30 mmol) in 6 mL of DMF at RT was added morpholine (1.2 mL, 13.20 mmol). The mixture was stirred 15 h at 50° C. under nitrogen. DMF was evaporated and the residue was partitioned between ethyl acetate (250 mL) and 1 N aqueous sodium bicarbonate (20 mL). The organic phase was washed with water (20 mL), brine (20 mL) and dried over MgSO₄. After evaporation the crude product was purified by column chromatography on silica (CH₂Cl₂:MeOH=98:2 to 97:3) to give benzyl L-threo-1-hydroxy-3-morpholino-1-phenylpropan-2-ylcarbamate as an oil (380 mg, 31% yield). The hydrochloride salt was obtained from 100 mg of the free base in diethylether at 0° C. using a solution 0.3 M HCl in diethylether. The precipitate was filtered and dry to give benzyl L-threo-1-hydroxy-3-morpholino-1-phenylpropan-2-ylcarbamate hydrochloride Compound 1 as a white solid (70 mg, 65% yield).

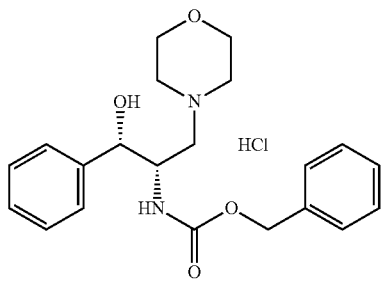

Compound 1

MW: 406.90; Yield: 20%; White Solid; Mp (° C.): 144.5.

$R_f$: 0.40 (CH₂Cl₂:MeOH=95:5).

¹H-NMR (CD₃OD,.): 3.14-3.77 (m, 6H, CH₂N), 3.70-4.07 (m, 4H, CH₂O), 4.30-4.33 (m, 1H, CH), 4.90-5.06 (m, 3H, CH, ArCH₂O), 7.20-7.43 (m, 10H, ArH).

¹³C-NMR (CD₃OD,.): 51.2, 51.8, 53.2, 59.3, 63.2, 66.3, 72.5, 125.8, 127.2, 127.3, 127.5, 127.8, 127.9.

MS-ESI m/z (% rel. Int.): 371.0 ([MH]⁺, 100).

HPLC: Method A, detection UV 254 nm, Compound 1 RT=4.40 min, peak area 96.5%.

$[\ ]^{22}_D$=+13.9 (c=1.00, MeOH).

L-threo-2-Amino-3-morpholino-1-phenylpropan-1-ol dihydrochloride Compound 2

To a stirred solution of benzyl L-threo-1-hydroxy-3-morpholino-1-phenylpropan-2-ylcarbamate Compound 1 (0.26 g, 0.70 mmol) in 20 mL of MeOH at RT was added Pd—C 10% (140 mg). The mixture was saturated with hydrogen and stirred for 24 h at RT under hydrogen atmosphere (balloon). The catalyst Pd—C 10% was removed by filtration on celite and the solution was evaporated. The crude product was purified by column chromatography on silica (CH₂Cl₂:MeOH:NH₄OH=79:20:1 to 75:20:5) to give L-threo-2-amino-3-morpholino-1-phenylpropan-1-ol as an oil (100 mg, 60% yield). The hydrochloride salt was obtained from 83 mg of the free base in diethylether at 0° C. using 0.3 M HCl in diethylether. After precipitation in diethylether, filtration and drying L-threo-2-amino-3-morpholino-1-phenylpropan-1-ol dihydrochloride Compound 2 was obtained as a white solid (80 mg, 74% yield).

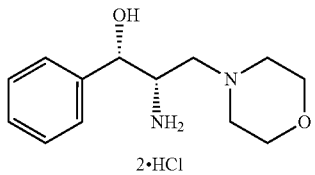

Compound 2

2·HCl

MW: 309.23; Yield: 44.0%; White Solid; Mp (° C.): 166.4-170.9.

$R_f$: 0.20 (CH₂Cl₂:MeOH=9:1).

¹H-NMR (CD₃OD,.): 3.30-3.77 (m, 6H, CH₂N), 3.92-4.05 (m, 4H, CH₂O), 4.05-4.16 (m, 1H, CH), 4.85-4.98 (m, 1H, CH), 7.35-7.60 (m, 5H, ArH).

¹³C-NMR (CD₃OD,.): 53.1, 54.9, 58.5, 64.8, 72.6, 127.2, 128.0, 130.2, 140.3.

MS-ESI m/z (% rel. Int.): 237.0 ([MH]⁺, 100).

HPLC: Method A, detection UV 254 nm, Compound 2 RT=0.90 min, peak area 98.0%.

$[\ ]^{22}_D$=+ 10.8 (c=1.00, MeOH), free base: $[\ ]^{22}_D$=−6.1 (c=0.25, CHCl₃).

Preparation of D-threo-2-amino-3-morpholino-1-phenylpropan-1-ol dihydrochloride Compound 4

(R)-Methyl 1-((S)-1-phenylethyl)aziridine-2-carboxylate EBE 06044B

To solution of methyl 2,3-dibromopropionate (25 mL, 198 mmol) in toluene at 5° C. was added triethylamine (55 mL, 0.39 mmol) in toluene (100 mL). After stirring for 5 min (S)-(1)-phenethylamine (25 mL, 198 mmol) in toluene (100 mL) was added dropwise. The suspension was refluxed for 3 h and allowed to cool down, filtered and the volatiles were evaporated under reduced pressure to give a residue that was purified by column chromatography (950 g of silica gel) with a gradient of 0-20% EtOAc in cyclohexane to yield to (S)-methyl 145)-1-phenylethyl)aziridine-2-carboxylate EBE 06044A as a yellow oil (17.31 g, 43% yield) and (R)-methyl 1-((S)-1-phenylethyl)aziridine-2-carboxylate EBE 06044B as a yellow oil (15.14 g, 37% yield).

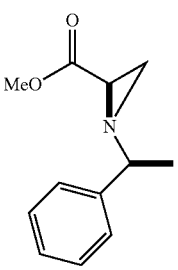

EBE 06044B

MW: 205.3; Yield EBE 06044B: 37%; Yellow Oil. Yield: EBE 06044A: 43%, Yellow Oil.

$R_f$: EBE 06044A=0.5; $R_f$: EBE 06044B=0.35 (EtOAc:cyclohexane=25:75).

¹H-NMR (CDCl₃) EBE 06044A: 1.47 (d, 3H, J=6.6 Hz, CH₃), 1.60 (d, 1H, J=6.4 Hz, CH), 2.13 (d, 1H, J=2.6 Hz), 2.21 (dd, 1H, J=3.2 Hz, J=6.4 Hz), 2.54 (q, 1H, J=6.6 Hz), 3.75 (s, 3H, OCH₃) 7.23-7.40 (m, 5H, ArH).

$^1$H-NMR (CDCl$_3$) EBE 06044B: 1.46 (d, 3H, J=6.6 Hz, CH$_3$), 1.79 (d, 1H, J=6.6 Hz, CH), 2.08 (d, 1H, J=3.11 Hz, 6.6 Hz), 2.34 (dd, 1H, J=3.1 Hz, J=1.0 Hz), 2.56 (q, 1H, J=6.6 Hz), 3.67 (s, 3H, OCH$_3$) 7.24-7.36 (m, 5H, ArH).

$^{13}$C-NMR (CDCl$_3$) EBE 06044B: 23.5, 35.0, 36.9, 52.2, 69.8, 126.5, 127.2, 128.5, 143.6, 171.1.

HPLC: Method A, detection at 254 nm, EBE 06044B RT=6.11 min, peak area 92.9%.

((R)-1-((S)-1-Phenylethyl)aziridin-2-yl)methanol EBE 06046

A 250 mL round bottom flask was charged with anhydrous THF (100 mL) and LiAlH$_4$ (2.77 g, 73.1 mmol). While the suspension is stirred at 0° C., a solution of (S)-methyl 1-((S)-1-phenylethyl)aziridine-2-carboxylate EBE 06044B (10.0 g, 48.7 mmol) in THF (50 mL) was added dropwise over 20 min. The dropping funnel was washed with THF (2×3 mL) and allowed to react 20 min at 0° C. Maintaining the reaction mixture at 0° C., a solution of KOH (10%, 20 mL) was added dropwise for 20 min (caution the reaction is exothermic). The mixture was stirred for 0.5 h at 25° C. and the white precipitate removed by filtration through a celite pad that was washed with diethyl ether (30 mL). The combined organic filtrates were washed with NaH$_2$PO$_4$ and the aqueous layer was extracted with Et$_2$O (3×30 mL). The combined organic phase were dried with Na$_2$SO$_4$ and concentrated to give ((R)-1-((S)-1-phenylethyl)aziridin-2-yl)methanol EBE 06046 as a white solid (10.4 g, 90% yield).

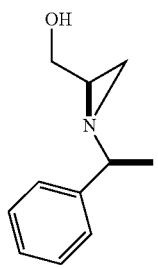

EBE 06046

MW: 177.2; Yield: 90%; White Solid; Mp (° C.): 37.7.

$^1$H-NMR (CDCl$_3$): 1.43 (d, 3H, J=6.6 Hz, CH$_3$), 1.49 (d, 1H, J=6.5 Hz, CH), 1.65-1.71 (m, 1H, CH), 1.92 (d, 1H, J=3.5 Hz, NCH), 2.26 (s, 1H, OH), 2.53 (q, 1H, J=6.6 Hz, NCH), 3.32-3.37 (m, 1H, OCH$_2$), 3.56 (m, 1H, OCH$_2$), 7.23-7.35 (m, 5H, ArH).

$^{13}$C-NMR (CDCl$_3$): 22.9, 31.4, 39.3, 62.5, 69.4, 126.6, 127.3, 128.6, 144.5.

(R)-1-((S)-1-Phenylethyl)aziridine-2-carbaldehyde EBE 06048

A three neck, 250 mL round bottom flask was equipped with a low temperature thermometer and two (2) equalizing dropping funnels. One of these was connected to a nitrogen line and charged with a solution of ((R)-1-((S)-1-phenylethyl)aziridin-2-yl)methanol EBE 06046 (7.0 g, 39.5 mmol) in CH$_2$Cl$_2$ (75 mL), the other was charged with a solution of DMSO (9.25 g, 118.5 mmol) in CH$_2$Cl$_2$ (11 mL). To a solution of oxalyl chloride (7.5 g, 59.3 mmol) in CH$_2$Cl$_2$ (90 mL) under N$_2$ at −78° C., the DMSO solution was added dropwise during 20 min and stirred for 20 min. EBE 06046 (7.0 g, 39.5 mmol) in CH$_2$Cl$_2$ (75 mL) was added dropwise over 50 min. then the dropping funnel was charged with DIEA (42.6 mL, 237 mmol) in CH$_2$Cl$_2$ (10 mL) and the reaction mixture was stirred for 30 min at −45° C. The DIEA solution was added over 5 min with the reaction mixture at −78° C. and the reaction was allowed to warm to room temperature. The reaction mixture was washed with H$_2$O (3×50 mL), dried over MgSO$_4$, filtered, evaporated. The crude product obtained was purified by column chromatography on silica with a gradient of 0-20% [v/v] EtOAc in cyclohexane to give (R)-1-((S)-1-phenylethyl)aziridine-2-carbaldehyde EBE 06048 as a yellow oil (5.59 g, 81% yield).

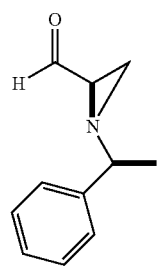

EBE 06048

MW: 175.2; Yield: 81%; Yellow Oil.

R$_f$: EBE 06048: 0.3 (EtOAc:cyclohexane=20:80).

$^1$H-NMR (CDCl$_3$): 1.47 (d, 3H, J=6.6 Hz, CH$_3$), 1.94 (d, 1H, J=6.7 Hz, NCH$_2$), 2.08 (dt, J=2.9 Hz, J=6.4 Hz, NCH), 2.37 (d, 1H, J=2.6 Hz, NCH$_2$), 2.61 (q, 1H, J=6.6 Hz, NCH), 7.20-7.38 (m, 5H, ArH), 8.92 (d, 1H, J=6.2 Hz).

$^{13}$C-NMR (CDCl$_3$): 22.7, 32.1, 43.2, 68.1, 125.5, 126.5, 127.6, 142.4, 198.7.

(R)-Phenyl((R)-1-((S)-1-phenylethyl)aziridin-2-yl)methanol EBE 06066

To a solution of bromobenzene (4.93 g, 31.4 mmol) in THF 125 mL under nitrogen at −78° was added t-BuLi (1.7 M in pentane, 50 mL). The mixture was stirred for 0.5 h at room temperature. The mixture was cooled down to −78° C. and a solution of (R)-1-((S)-1-phenylethyl)aziridine-2-carbaldehyde EBE 06048 (2.5 g, 14.3 mmol) in THF (16.7 mL) at −78° C. was added dropwise. The reaction mixture was treated with H$_2$O (20 mL), the organic layer was separated and the aqueous phase was extracted with EtOAc. The combined organic layers were dried over MgSO$_4$, filtered and concentrated in vacuo to give a residue that was purified by column chromatography using a gradient of 0-20% [v/v] EtOAc in cyclohexane to give (R)-phenyl((R)-1-((S)-1-phenylethyl)aziridin-2-yl)methanol EBE 06066 (3.13 g, 86% yield).

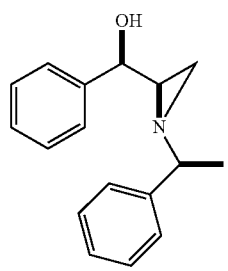

EBE 06066

MW: 253.3; Yield: 86%.

R$_f$ =0.3 (EtOAc:cyclohexane=20:80).

$^1$H-NMR (CDCl$_3$): 1.47 (d, 3H, J=6.6 Hz, CH$_3$), 1.57 (d, 1H, J=6.5 Hz, CH), 1.79 (dt, 1H, J=3.5 Hz, J=8.7 Hz, CH), 2.04 (d, 1H, J=3.5 Hz, OCH), 2.35 (bs, 1H, OH), 2.53 (q, 1H, J=6.5 Hz, CH), 4.23 (d, 1H, J=5.7 Hz, OCH), 7.07-7.13 (m, 2H, ArH), 7.16-7.20 (m, 3H, ArH), 7.24-7.34 (m, 5H, ArH).

$^{13}$C-NMR (CDCl$_3$): 22.4, 32.0, 44.6, 69.4, 74.1, 125.8 (2×C), 126.9 (2×C), 127.3, 127.6, 128.2 (2×C), 128.7 (2×C), 142.0, 144.2.

[ ]$^{22}_D$=−71.53 (c=0.59, CHCl$_3$).

D-threo-2-((S)-1-Phenylethylamino)-3-morpholino-1-phenylpropan-1-ol dihydrochloride Compound 5

To a solution of (R)-phenyl((R)-1-((S)-1-phenylethyl) aziridin-2-yl)methanol EBE 06066 (1.5 g, 5.92 mmol) in CH$_3$CN (19 mL) at RT was added iodotrimethylsilane (3.55 g, 17.8 mmol). The solution was stirred for 2 h and morpholine (1.032 g, 11.84 mmol) was added. After 2 h at reflux, the reaction mixture was treated with HCl (1M) to reach pH=1 and stirred for 10 min. After a slow addition of NaHCO$_3$ to reach pH=9, the product was extracted with EtOAc, dried over Na$_2$SO$_4$, filtered to give after evaporation a crude brown oil that was purified by column chromatography using a gradient of 0-20% [v/v] MeOH in EtOAc to give D-threo-2-((S)-1-phenylethylamino)-3-morpholino-1-phenylpropan-1-ol EBE 06068A (0.831 g, 42%) as a pale brown solid. To a solution of D-threo-2-((S)-1-phenylethylamino)-3-morpholino-1-phenylpropan-1-ol EBE 06068A (0.100 g, 0.294 mmol) in ethanol (1 mL) was added a solution of HCl (0.8 M, 0.816 mL) in EtOH. Evaporation of the volatiles afforded to D-threo-2-((S)-1-phenylethylamino)-3-morpholino-1-phenylpropan-1-ol dihydrochloride Compound 5 as white solid (0.125 g, 100%).

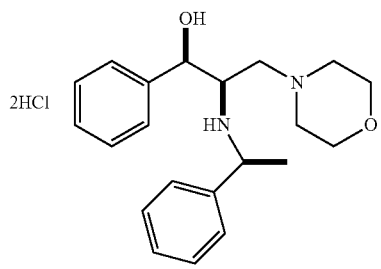

Compound 5

MW: 412.37; Yield: 42%; White Solid; Mp (° C.): 157.2 (dec).

R$_f$: 0.3 (MeOH:EtOAc=20:80) EBE 06068A.

$^1$H-NMR (CD$_3$OD,.): 1.19 (t, 2H, J=7.0 Hz, NCH$_2$), 1.71 (d, 3H, J=6.8 Hz, CH$_3$), 3.45 (m, 2H, J=7.1 Hz, NCH$_2$), 3.62 (q, 2H, J=7.1 Hz, N—CH$_2$), 3.97 (t, 4H, J=4.5 Hz, OCH$_2$), 4.06 (m, 1H, CH—N), 4.75 (q, 1H, J=6.8 Hz, CH—N), 5.21 (d, 1H, J=5.1 Hz, CH—O), 7.44-7.56 (m, 10H, ArH).

MS-ESI m/z (% rel. Int.): 341.1 ([MH]$^+$, 20).

$^{13}$C-NMR (CD$_3$OD,.): 24.4, 54.5 (2×C), 55.5, 55.9, 60.0, 67.0 (2×C), 75.6, 126.3 (2×C), 126.5 (2×C), 127.0, 127.1, 128.1 (2×C), 128.5 (2×C), 142.2, 145.3.

HPLC: Method A, detection at 254 nm, Compound 5 RT=4.41 min, peak area 99%.

D-threo-2-Amino-3-morpholino-1-phenylpropan-1-ol dihydrochloride Compound 4

To a solution of D-threo-2-((S)-1-phenylethylamino)-3-morpholino-1-phenylpropan-1-ol EBE 06068A (0.400 g, 1.17 mmol) in MeOH (6 mL) at RT was added acetic acid (0.133 mL, 2.35 mmol). The reaction vessel was flushed with nitrogen and Pd(OH)$_2$ (25% weight, 0.150 g) was added. The nitrogen atmosphere was exchanged with hydrogen using three cycle of vacuum and hydrogen addition using a balloon of hydrogen. After stirring for 16 hours under hydrogen the reaction mixture was filtrated through celite to give EBE 06070A the acetate salt of (2R)-amino-3-morpholin-4-yl-(1R)-phenyl-propan-1-ol (0.279 g, 98% yield). To as solution of EBE 06070A the acetate salt of (2R)-amino-3-morpholin-4-yl-(1R)-phenyl-propan-1-ol (0.100 g, 0.338 mmol) in ethanol (1 mL) was added a solution of HCl (0.8 M, 0.930 mL) in EtOH. Evaporation of the volatiles afforded to D-threo-2-amino-3-morpholino-1-phenylpropan-1-ol dihydrochloride Compound 4 (0.104 g, 100% yield) as an off white solid. (Adapted from Shin, S-H.; Han, E. Y.; Park, C. S.; Lee, W. K.; Ha, H.-J. *Tetrahedron Asymmetry*, 2000, 11, 3293-3301).

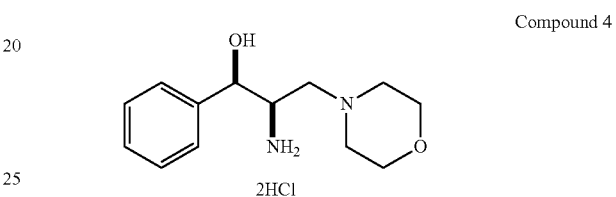

Compound 4

MW: 309.23; Yield: 99%; Off White Solid; Mp (° C.): 183.4.

$^1$H-NMR (CD$_3$OD,.): 3.30-3.77 (m, 6H, CH$_2$N), 3.92-4.05 (m, 4H, CH$_2$O), 4.05-4.16 (m, 1H, CH), 4.85-4.98 (m, 1H, CH), 7.35-7.60 (m, 5H, ArH).

$^{13}$C-NMR (CD$_3$OD,): 53.2, 58.3, 58.5 (2×C), 64.9 (2×C), 72.6, 128.0 (2×C), 130.2 (2×C), 140.3.

MS-ESI m/z (% rel. int.): 237.1 (100, [MH]$^+$).

HPLC: Isocratic 10% CH$_3$CN in H$_2$O (pH 10, [NH$_4$OH]=5 mM), detection UV 254 nm, Compound 4 RT=6.63 min, peak area 97.3%.

[ ]$^{22}_D$=−10.7 (c=1.00, MeOH).

Preparation of Compound 13, Compound 14, Compound 15, Compound 16 and Compound 17

Method B:

To a stirred and cooled (0° C.) solution of potassium hydroxide (380 mg, 5.80 mmol) in MeOH (5 mL) were added successively aldehyde (5.80 mmol) and 2-isocyano-1-(pyrrolidin-1-yl)ethanone BLE 04098 (0.8 g, 5.8 mmol). The solution was stirred 3 h at 0° C. and then concentrated. The residue was partitioned between CH$_2$Cl$_2$ (100 mL) and water. The organic layer was washed with brine, dried over MgSO$_4$, filtered and evaporated. Concentration afford to a crude product which was purified by column chromatography on silica (cyclohexane:EtOAc=70/30 to 0:100) to yield, after evaporation and drying, to an intermediate oxazoline. To a stirred solution of oxazoline in methanol (15 mL) was added hydrochloric acid (1 mL, 12 mmol). After heating at 60° C. for 2 h, the mixture reaction was then concentrated and the resulting yellow oil was coevaporated twice with MeOH before solidifying. Triturated in EtOAc:MeOH=10/1 followed by filtration gave title compound as a white solid.

DL-threo-2-Amino-3-hydroxy-3-(4-methoxyphenyl)-1-(pyrrolidin-1-yl)propan-1-one hydrochloride Compound 13

The compound was prepared according to method B with 4-methoxybenzaldehyde (811 mg, 5.80 mmol). DL-threo-2-

Amino-3-hydroxy-3-(4-methoxyphenyl)-1-(pyrrolidin-1-yl)propan-1-one hydrochloride Compound 13 was obtained as a white solid (468 mg, 30% yield).

Compound 13

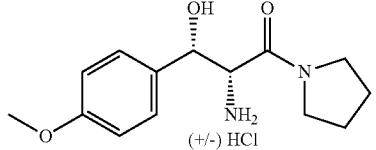
(+/-) HCl

MW: 300.78; Yield: 30.0%; White Solid; Mp (° C.): 176.6. $R_f$: 0.15 (EtOAc:MeOH=85:15) free base.
$^1$H-NMR (CD$_3$OD,.): 1.37-1.78 (m, 4H, 2×CH$_2$), 2.17-2.25 (m, 1H, CH$_2$N), 3.15-3.26 (m, 2H, CH$_2$N), 3.34-3.40 (m, 2H, CH$_2$N), 3.79 (s, 3H, CH$_3$O), 4.06 (d, 1H, J=9.3 Hz, CH—N), 4.80 (d, 1H, J=9.3 Hz, CH—O), 6.94 (m, 2H, J=8.7 Hz, ArH), 7.33 (d, 2H, J=8.6 Hz, ArH).
$^{13}$C-NMR (CD$_3$OD,.): 24.8, 26.6, 47.2, 47.6, 55.9, 59.6, 73.8, 115.0, 128.9, 132.5, 161.7, 166.4.
MS-ESI m/z (% rel. Int.): 265.1 ([MH]$^+$, 10), 247.1 (100).
HPLC: Method A, detection UV 254 nm, Compound 13 RT=3.70 min, peak area 99.00%.

DL-threo-2-Amino-3-(4-chlorophenyl)-3-hydroxy-1-(pyrrolidin-1-yl)propan-1-one hydrochloride Compound 14

The compound was prepared according to method B with 4-chlorobenzaldehyde (837 mg, 5.80 mmol). DL-threo-2-Amino-3-(4-chlorophenyl)-3-hydroxy-1-(pyrrolidin-1-yl)propan-1-one hydrochloride Compound 14 was obtained as a white solid (483 mg, 33% yield).

Compound 14

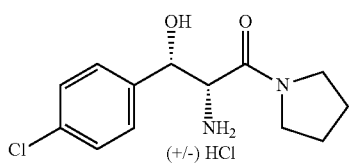
(+/-) HCl

MW: 321.24; Yield: 33.0%; White Solid; Mp (° C.): 190.1. $R_f$: 0.15 (EtOAc:MeOH=85:15), free base.
$^1$H-NMR (CD$_3$OD,.): 1.41-1.78 (m, 4H, 2×CH$_2$), 2.24-2.32 (m, 1H, CH$_2$N), 3.16-3.28 (m, 2H, CH$_2$N), 3.34-3.40 (m, 1H, CH$_2$N), 4.11 (d, 1H, J=9.0 Hz, CH—N), 4.85-4.88 (m, 1H, CH—O), 7.42 (s, 4H, ArH).
$^{13}$C-NMR (CD$_3$OD,.): 24.8, 26.6, 47.2, 47.6, 59.2, 73.5, 129.4, 129.8, 135.8, 139.6, 166.1.
MS-ESI m/z (% rel. Int.): 269.1/271.1 ([MH]$^+$, 50/20), 251.1/253.1 (100/30).
HPLC: Method A, detection UV 254 nm, Compound 14 RT=4.00 min, peak area 99.00%.

DL-threo-2-Amino-3-(3,4-dichlorophenyl)-3-hydroxy-1-(pyrrolidin-1-yl)propan-1-one hydrochloride Compound 15

The compound was prepared according to method B with 3,4-dichlorobenzaldehyde (809 mg, 4.60 mmol). DL-threo-2-Amino-3-(3,4-dichlorophenyl)-3-hydroxy-1-(pyrrolidin-1-yl)propan-1-one hydrochloride Compound 15 was obtained as a white solid (522 mg, 31% yield).

Compound 15

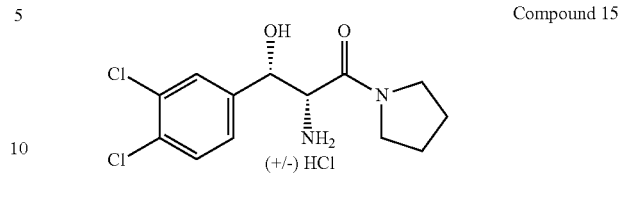
(+/-) HCl

MW: 355.69; Yield: 31.0%; White Solid; Mp (° C.): 186.3. $R_f$: 0.15 (EtOAc:MeOH=85:15), free base.
$^1$H-NMR (CD$_3$OD,.): 1.46-1.82 (m, 4H, 2×CH$_2$), 2.32-2.40 (m, 1H, CH$_2$N), 3.20-3.27 (m, 1H, CH$_2$N), 3.34-3.43 (m, 2H, CH$_2$N), 4.15 (d, 1H, J=8.7 Hz, CH—N), 4.87-4.90 (m, 1H, CH—O), 7.38 (dd, 1H, J=8.3 Hz, J=1.7 Hz, ArH), 7.57-7.59 (m, 2H, ArH).
$^{13}$C-NMR (CD$_3$OD,.): 24.9, 26.7, 47.3, 47.8, 59.0, 72.8, 127.5, 129.8, 131.9, 133.6, 133.7, 141.6, 166.0.
MS-ESI m/z (% rel. Int.): 303.1/305.0 ([MH]$^+$, 65/45), 111.0 (100).
HPLC: Method A, detection UV 254 nm, Compound 15 RT=4.20 min, peak area 99.00%.

DL-threo-2-Amino-3-hydroxy-3-phenyl-1-(pyrrolidin-1-yl)propan-1-one hydrochloride Compound 16

The compound was prepared according to method B with benzaldehyde (0.613 g, 5.78 mmol). DL-threo-2-Amino-3-hydroxy-3-phenyl-1-(pyrrolidin-1-yl)propan-1-one hydrochloride Compound 16 was obtained as a white solid (0.225 g, 14% yield).

Compound 16

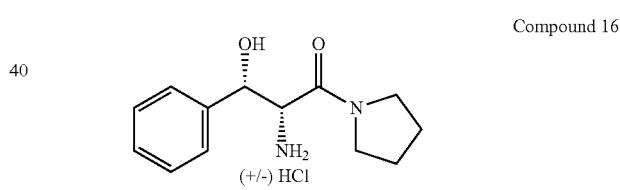
(+/-) HCl

MW: 270.76; Yield: 14%; White Solid; Mp (° C.): 184.9.
$^1$H-NMR (CD$_3$OD,.): 1.30-1.42 (m, 1H, CH$_2$), 1.50-1.60 (m, 1H, CH$_2$), 1.60-1.80 (m, 2H, CH$_2$), 2.05-2.15 (m, 1H, CH$_2$), 3.12-3.30 (m, 2H, NCH$_2$), 3.30-3.40 (m, 1H, NCH$_2$), 4.09 (d, 1H, J=9.2 Hz, CH—N), 4.80-4.95 (m, 1H, CH—O), 7.30-7.45 (m, 5H, ArH).
$^{13}$C-NMR (CD$_3$OD,.): 24.7, 26.5, 47.2, 47.5, 59.5, 74.2, 127.7, 129.7, 130.0, 140.8, 166.3.
MS-ESI m/z (% rel. Int.): 235.2 ([MH]$^+$, 100).
HPLC: Method A, detection UV 254 nm, Compound 16 RT=3.56 min, peak area 96.4%.

DL-threo-2-Amino-3-hydroxy-1-(pyrrolidin-1-yl)-3-p-tolylpropan-1-one hydrochloride Compound 17

The compound was prepared according to method B with 4-methyl-benzaldehyde (0.694 g, 5.78 mmol). DL-threo-2-Amino-3-hydroxy-1-(pyrrolidin-1-yl)-3-p-tolylpropan-1-one hydrochloride Compound 17 was obtained as a white solid (0.044 g, 3% yield).

Compound 17

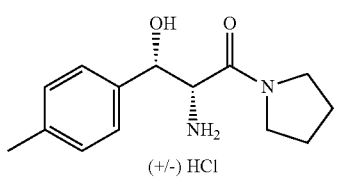
(+/-) HCl

MW: 284.78; Yield: 3%; White Solid; Mp (° C.): 184.2.

$^1$H-NMR (CD$_3$OD,.): 1.28-1.40 (m, 1H, CH$_2$), 1.50-1.60 (m, 1H, CH$_2$), 1.60-1.80 (m, 2H, CH$_2$), 2.10-2.22 (m, 1H, CH$_2$), 2.34 (s, 3H, CH$_3$), 3.10-3.25 (m, 2H, NCH$_2$), 3.25-3.40 (m, 1H, NCH$_2$), 4.07 (d, 1H, J=9.2 Hz, CH—N), 4.80 (d, 1H, J=9.2 Hz, CH—O), 7.21 (d, 2H, J=8.1 Hz, ArH), 7.30 (d, 2H, J=8.0 Hz, ArH)

$^{13}$C-NMR (CD$_3$OD,.): 21.2, 24.8, 26.5, 47.2, 47.5, 59.6, 74.1, 127.6, 130.2, 137.7, 140.1, 166.4.

MS-ESI m/z (% rel. Int.): 249.2 ([MH]$^+$, 30).

HPLC: Method A, detection UV 254 nm, Compound 17 RT=3.90 min, peak area 99.9%.

1-Phenyl-2-decanoylamino-3-morpholino-1-propanol (PDMP) Isomers and Enantiomers

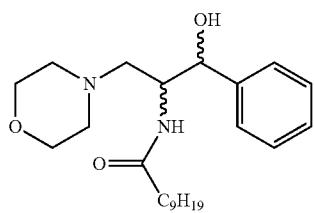
PDMP
mixture of DL-erythro and
DL-threo isomers

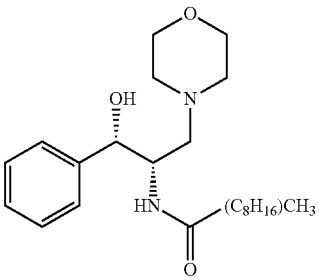
L-threo-PDMP

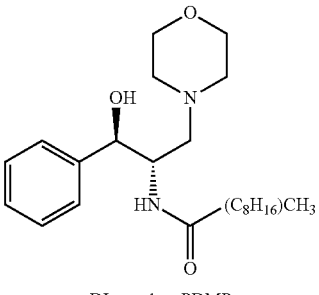
DL-erythro-PDMP

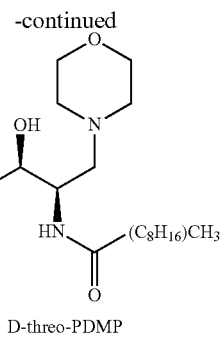
D-threo-PDMP

The above shown isomers and enantiomers, as applicable, of 1-phenyl-2-decanoylamino-3-morpholino-1-propanol (PDMP) are available commercially from Matreya, LLC, and can be prepared in accordance with the applicable references described in the background art section of the present application. Specifically, preparation of PDMP is described in Inokuchi, J. et al., *J. Lipid Res.* 28, 565-571, 1987; Radin, A. et al., *NeuroProtocols,* 3(2), 145-55, 1993; Radin, A. et al., *J. Lipid Res.* 36, 611-621, 1995 and U.S. Pat. No. 5,916,911 which are incorporated herein by reference. Enantiomerically pure D-threo-PDMP has been reported by Mitchell, Scott A. [*J. Org. Chem.,* 63 (24), 8837-8842, 1998]; Miura, T. et al, [*Bioorg. Med. Chem.,* 6, 1481-1498, 1998]; Shin, S. et al., [*Tetrahedron asymmetry,* 11, 3293-3301, 2000]; WO 2002012185 which are incorporated herein by reference. Synthesis of enantiomerically pure L-threo-PDMP is described by Mitchell, Scott A., [*J. Org. Chem.,* 63 (24), 8837-8842, 1998]; Miura, T. et al, [*Bioorg. Med. Chem.,* 6, 1481-1498, 1998]; and JP-A-9-216858, which are incorporated herein by reference.

What is claimed is:

1. A method of treating pain in a mammal in need of such treatment, comprising administering to said mammal a compound selected from the group consisting of the compounds shown by structural formulas below

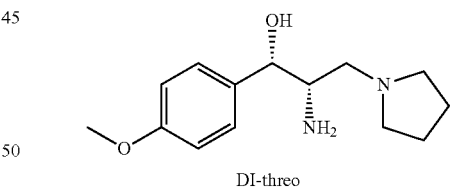
Dl-threo

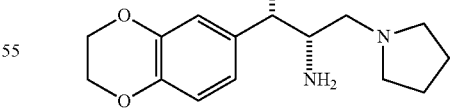
DL-threo

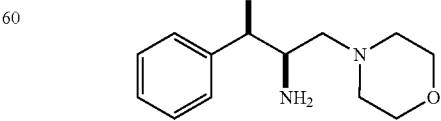
2 HCl
D-threo

-continued

[Structure: 3-hydroxy-2-amino-3-phenyl-1-(pyrrolidin-1-yl)propan-1-one]
HCl
DL-threo

[Structure: 3-hydroxy-2-amino-3-(4-methylphenyl)-1-(pyrrolidin-1-yl)propan-1-one]
HCl
DL-threo

[Structure: 3-hydroxy-2-amino-3-(4-methoxyphenyl)-1-(pyrrolidin-1-yl)propan-1-one]
HCl
DL-threo

[Structure: 3-hydroxy-2-amino-3-(4-chlorophenyl)-1-(pyrrolidin-1-yl)propan-1-one]
HCl
DL-threo

[Structure: 3-hydroxy-2-amino-3-(3,4-dichlorophenyl)-1-(pyrrolidin-1-yl)propan-1-one]
HCl
DL-threo

[Structure: 2-amino-3-morpholino-1-phenylpropan-1-ol]
2 HCl
DL-threo

-continued

[Structure: 2-amino-3-morpholino-1-phenylpropan-1-ol, L-threo]
2 HCl
L-threo or any pharmaceutically acceptable salt thereof.

2. A method in accordance with claim 1 wherein the compound has the formula

[Structure: 2-amino-1-(2,3-dihydrobenzo[b][1,4]dioxin-6-yl)-3-(pyrrolidin-1-yl)propan-1-ol]
DL-threo or any pharmaceutically acceptable salt thereof.

3. A method in accordance with claim 1 wherein the compound has the formula

[Structure: 2-amino-3-morpholino-1-phenylpropan-1-ol, D-threo]
2 HCl
D-threo or any other pharmaceutically acceptable salt of said compound.

4. A method in accordance with claim 1 wherein the compound has the formula

[Structure: 2-amino-3-morpholino-1-phenylpropan-1-ol]
HCl
DL-threo or any other pharmaceutically acceptable salt of said compound.

5. A method in accordance with claim 1 wherein the compound has the formula

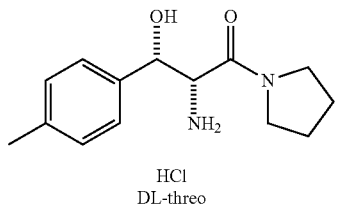 [SMILES: Cc1ccc([C@H](O)[C@@H](N)C(=O)N2CCCC2)cc1]

HCl
DL-threo or any other pharmaceutically acceptable salt of said compound.

6. A method in accordance with claim 1 wherein the compound has the formula

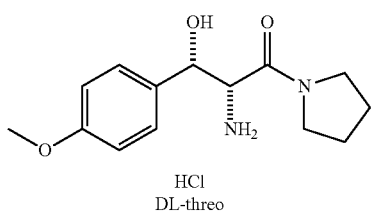 [SMILES: COc1ccc([C@H](O)[C@@H](N)C(=O)N2CCCC2)cc1]

HCl
DL-threo or any other pharmaceutically acceptable salt of said compound.

7. A method in accordance with claim 1 wherein the compound has the formula

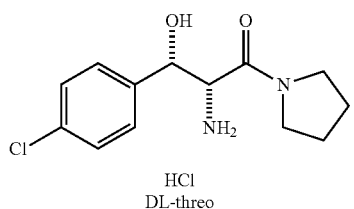 [SMILES: N[C@@H](C(=O)N1CCCC1)[C@@H](O)c1ccc(Cl)cc1]

HCl
DL-threo or any other pharmaceutically acceptable salt of said compound.

8. A method in accordance with claim 1 wherein the compound has the formula

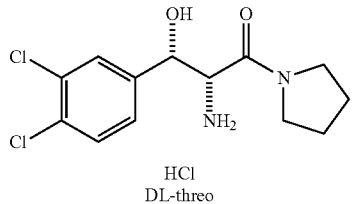 [SMILES: N[C@@H](C(=O)N1CCCC1)[C@@H](O)c1ccc(Cl)c(Cl)c1]

HCl
DL-threo or any other pharmaceutically acceptable salt of said compound.

9. A method in accordance with claim 1 wherein the compound has the formula

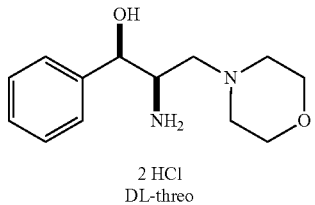 [SMILES: N[C@H](CN1CCOCC1)[C@H](O)c1ccccc1]

2 HCl
DL-threo or any other pharmaceutically acceptable salt of said compound.

10. A method in accordance with claim 1 wherein the compound has the formula

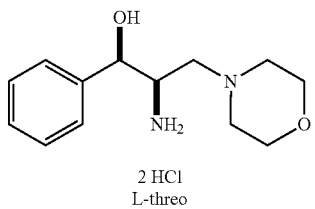 [SMILES: N[C@H](CN1CCOCC1)[C@H](O)c1ccccc1]

2 HCl
L-threo or any other pharmaceutically acceptable salt of said compound.

11. A method in accordance with claim 1 wherein said pain is chronic pain.

12. A method in accordance with claim 11, wherein said chronic pain results from peripheral neuropathy.

* * * * *